(12) United States Patent
Gao et al.

(10) Patent No.: US 8,076,501 B2
(45) Date of Patent: *Dec. 13, 2011

(54) PHOTOGENERATED REAGENTS

(76) Inventors: Xiaolian Gao, Houston, TX (US); Zhuo Xiaochruan, Houston, TX (US); Wu Yao, Houston, TX (US); Jean-Phillipe Pollols, College Station, TX (US)

( * ) Notice: Subject to any disclaimer, the term of this patent is extended or adjusted under 35 U.S.C. 154(b) by 260 days.

This patent is subject to a terminal disclaimer.

(21) Appl. No.: 12/454,471

(22) Filed: May 18, 2009

(65) Prior Publication Data

US 2010/0137600 A1 Jun. 3, 2010

Related U.S. Application Data

(60) Division of application No. 11/648,717, filed on Dec. 29, 2006, now Pat. No. 7,544,829, which is a continuation of application No. 11/242,622, filed on Oct. 3, 2005, now Pat. No. 7,235,670, which is a continuation of application No. 10/701,135, filed on Nov. 4, 2003, now Pat. No. 6,965,040.

(60) Provisional application No. 60/423,680, filed on Nov. 4, 2002.

(51) Int. Cl.
*C07C 69/76* (2006.01)
(52) U.S. Cl. ...................................................... 560/103
(58) Field of Classification Search .................. 560/103
See application file for complete search history.

(56) References Cited

U.S. PATENT DOCUMENTS 6,965,040 B1 * 11/2005 Gao et al. ...................... 549/439
7,235,670 B2 * 6/2007 Gao et al. ...................... 548/255

* cited by examiner

*Primary Examiner* — Taofiq A Solola
(74) *Attorney, Agent, or Firm* — G Kenneth Smith

(57) ABSTRACT

This invention describes reagent precursors and methods for chemical and biochemical reactions. These reagent precursors that can be activated in solution upon irradiation to generate reagents required for the subsequent chemical reactions. Specifically, photogenerated reagents (PGR) are useful for controlling parallel combinatorial synthesis and various chemical and biochemical reactions.

16 Claims, 15 Drawing Sheets

FIG 1A

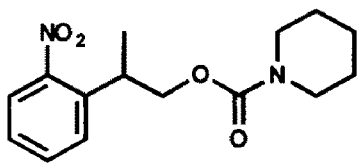

2-(2-nitrophenyl)propoxycarbonyl piperidine (NPPOC-pip)

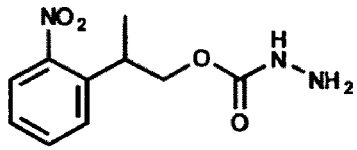

2-(2-nitrophenyl)propoxycarbonyl hydrazine (NPPOC-Hz)

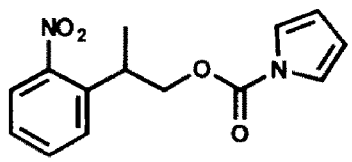

2-(2-nitrophenyl)propoxycarbonyl tetrazole (NPPOC-taz)

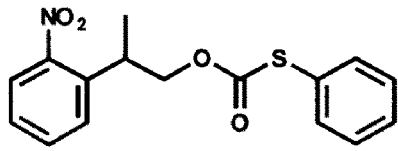

2-(2-nitrophenyl)propoxycarbonyl thiophenol (NPPOC-SPh)

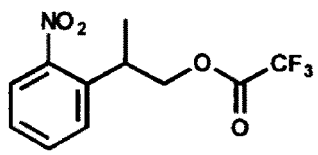

2-(2-nitrophenyl)propyl trifluoroacetate (NPPO-TFA)

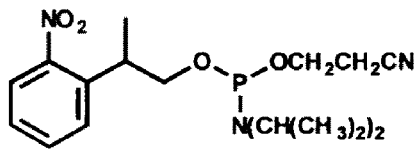

2-(2-nitrophenyl)propoxyl b-cyanoethyl diisopropyl phosphoramidite (NPPO-ppa)

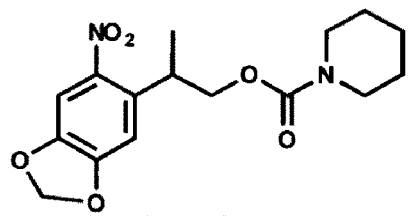

7.2-(3,4-methylenedioxy-6-nitrophenyl)-propoxycarbonyl piperidine

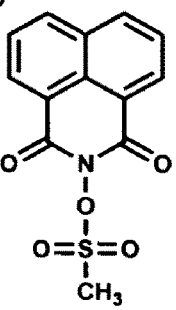

N-methylsufonyloxynaphthalimide (NAI-MSA)

FIG 1B
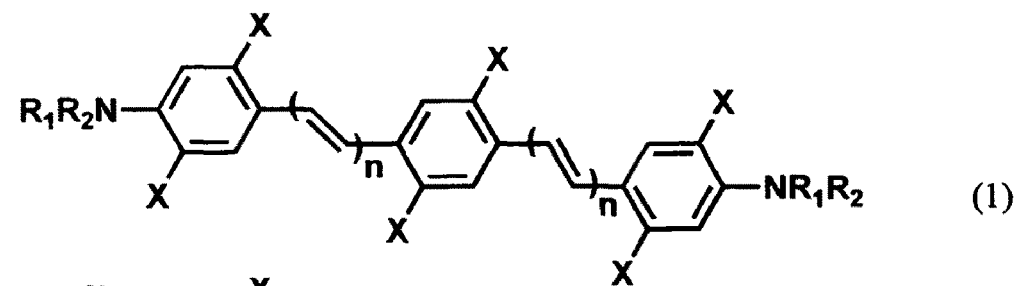
(1)
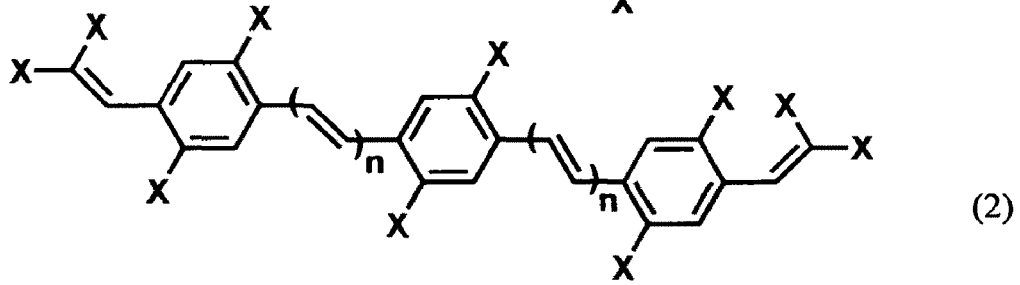
(2)
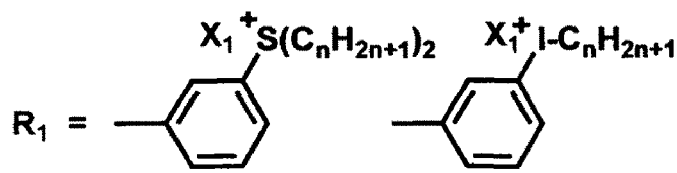
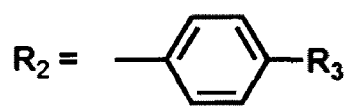
$R_3$ = H, $C_nH_{2n+1}$, $OR_4$ ($R_4$ = $C_nH_{2n+1}$), and other typical aromatic substituents
n = 1 - 5
X = H, $OR_4$, CN, Cl, Br, I, $C(O)N(R_4)_2$, or other typical aromatic substituents
$X_1$ = $SbF_6^-$, $PF_6^-$, $B(PhF_5)_4^-$, 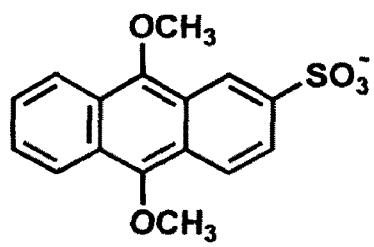

FIG 1C

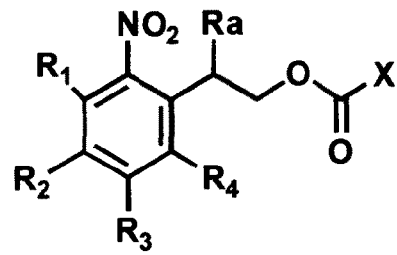

(1)

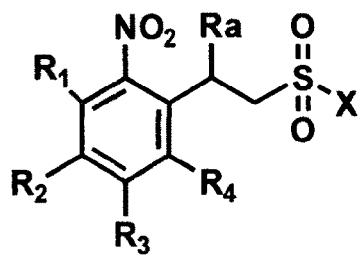

(2)

$R_{1-4}$ = H, Cl, Br, $NO_2$, $CF_3$, CN, OMe, $OCH_2O$, Ph, benzyl, O-benzyl, or alkyl, or, aryl, or alkylaryl, or akoxyalkyl having 1-12 carbons;

Ra = H, $CH_3$, Cl, Br, phenyl, acetyl, or acyl, or alkyl, or alkylaryl, or akoxyalkyl having 1-12 carbons;

X = N(alkyl)$_2$, or N(cyclic alkyl), or O(alkyl), or S(alkyl) (having 1-12 carbon atoms, or having alkyl with substitutions of halogen atoms), N(aryl)$_2$, or N(cyclic aryl), or O(aryl), or S(aryl) (having 1-12 carbon atoms, or having aryl with substitutions of halogen atoms), HNNH2, tetrazoloyl.

FIG 4A
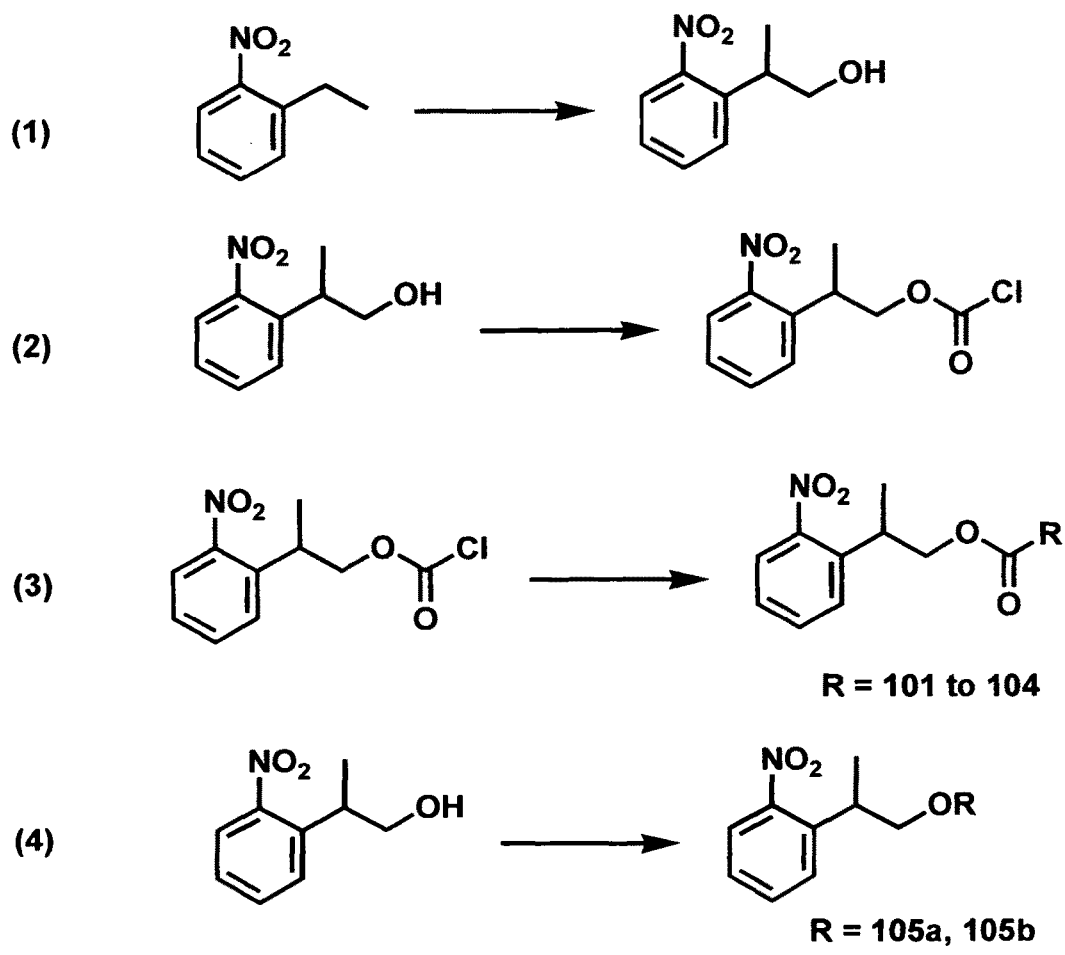
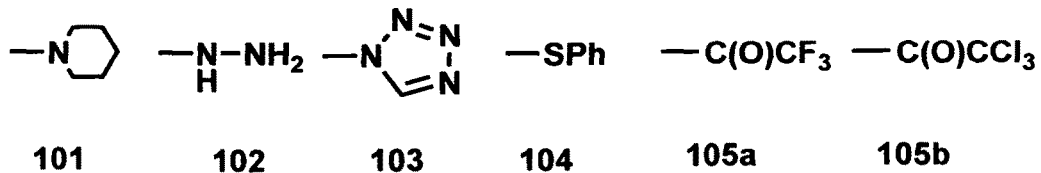

FIG 5
Photolytic generation of chemicla reagents
(1) PGR-P $\xrightarrow{h\nu}$ PGR     PGR-P: photogenerated reagent precursor
PGR: photogenerated reagent
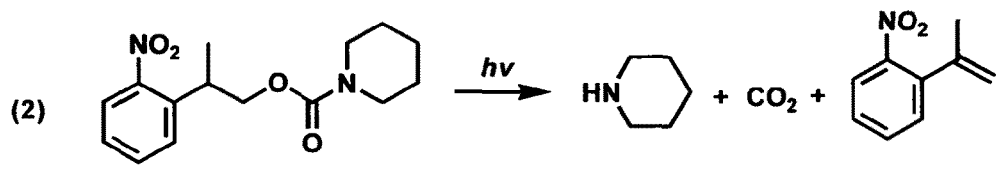
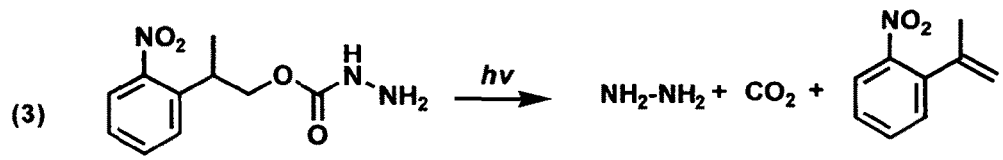
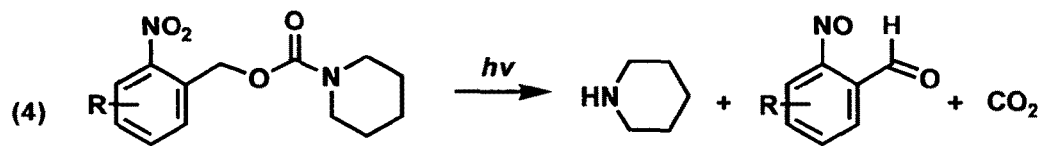
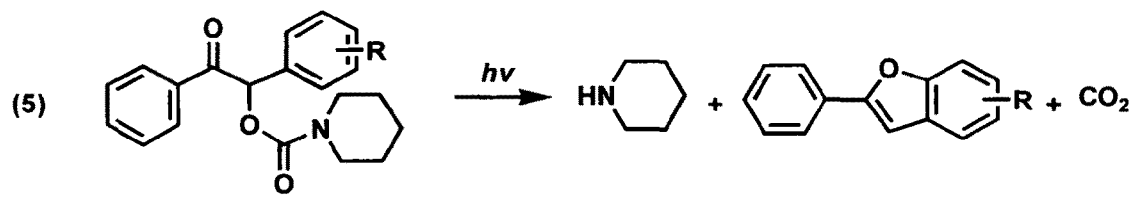

PHOTOGENERATED REAGENTS

RELATED U.S. APPLICATION DATA

This is a divisional application of U.S. application Ser. No. 11/648,717 filed on Dec. 29, 2006 now U.S. Pat. No. 7,544,829, which is a continuation of Ser. No. 11/242,622 filed Oct. 3, 2005 now U.S. Pat. No. 7,235,670 which is a continuation U.S. application Ser. No. 10/701,135 filed Nov. 4, 2003 now U.S. Pat. No. 6,965,040 which claims priority to U.S. Provisional Application No. 60/423,680 filed Nov. 4, 2002.

STATEMENT REGARDING FEDERALLY SPONSORED RESEARCH OR DEVELOPMENT

Rights to inventions in part made under the sponsored research by National Institutes of Health (R01 GM49957).

BACKGROUND OF THE INVENTION

The present invention relates to the field of chemical and biochemical reactions. More specifically, the present invention relates to the use of photogenerated reagents (PGR) for use in parallel synthesis and assay of a plurality of organic and bio-organic molecules on a substrate surface in accordance with a predetermined spatial distribution pattern. Methods and apparatus of the present invention are useful for preparing and assaying very-large-scale arrays of DNA and RNA oligonucleotides, peptides, oligosaccharides, phospholipids and other biopolymers and biological samples on a substrate surface.

Development of modern medicine, agriculture, and materials imposes enormous demands on technological and methodological progress to accelerate sample screening in chemical and biological analysis. Development of parallel processes on a micro-scale is critical to the progress. Many advances have been made in this area using parallel synthesis, robotic spotting, inkjet printing, and microfluidics (Marshall et al., Nature Biotechnol. 16, 27-31 (1998)). Continued efforts are sought for more reliable, flexible, faster, and inexpensive technologies.

For high-throughput screening applications, a promising approach is the use of molecular microarray (MMA) chips, specifically biochips containing high-density arrays of biopolymers immobilized on solid surfaces. These biochips are becoming powerful tools for exploring molecular genetic and sequence information (Marshall et al., Nature Biotechnol. 16, 27-31 (1998) and Ramsay, Nature Biotechnol. 16, 40-44 (1998)). Target molecules have been hybridized to DNA oligonucleotides and cDNA probes on biochips for determining nucleotide sequences, probing multiplex interactions of nucleic acids, identifying gene mutations, monitoring gene expression, and detecting pathogens (Schena, et al., Science 270, 467-460 (1995); Lockhart et al., Nature Biotechnol. 14, 1675-1680; Weiler, Nucleic Acids Res. 25, 2792-2799 (1997); de Saizieu et al., Nature Biotechnol. 16, 45-48 (1998); Drmanc et al., Nature Biotechnol. 16, 54-58 (1998)). The continued development of biochip technology will have a significant impact on the fields of biology, medicine, and clinical diagnosis.

Light-directed on-chip parallel synthesis has been used in the fabrication of very-large-scale oligonucleotide arrays with up to one million sequences on a single chip. Two major methods have been disclosed: synthesis using photolabile-group protected monomers (Pirrung et al., U.S. Pat. No. 5,143,854 (1992); Fodor et al., U.S. Pat. No. 5,424,186 (1995)) and synthesis using chemical amplification chemistry (Beecher et al., PCT Publication No. WO 98/20967 (1997)). Both methods involve repetitive steps of deprotection, monomer coupling, oxidation, and capping. Photomasks are used to achieve selective light exposure in predetermined areas of a solid substrate surface, on which oligonucleotide arrays are synthesized.

For the synthesis process involving photolabile-protecting groups, the photolabile-protecting groups are cleaved from the reactant, i.e., the 5'-O of the growing oligonucleotide molecules in illuminated surface areas while in non-illuminated surface areas the protecting groups on oligonucleotide molecules are not affected. The substrate surface is subsequently contacted with a solution containing monomers having an unprotected first reactive center and a second reactive center protected by a photolabile-protecting group. In the illuminated surface areas, monomers couple via the unprotected first reactive center with the deprotected oligonucleotide molecules. However, in the non-illuminated surface areas oligonucleotides remain protected with the photolabile-protecting groups and, therefore, no coupling reaction takes place. The resulting oligonucleotide molecules after the coupling are protected by photolabile protecting groups on the second reactive center of the monomer. Therefore, one can continue the above photo-activated chain propagation reaction until all desired oligonucleotides are synthesized.

There are significant drawbacks in the method involving photolabile-protecting groups: (a) the chemistry used is non-conventional and the availability of building blocks is limited (only DNA oligonucleotides are now routinely made); (b) the method is not applicable to the synthesis of other types of organic molecules due to the unavailability of the photolabile protected building blocks; (c) the method suffers from low sequence fidelity due to inherent low efficiency of the photo-reaction used and requirement of 100% deprotection efficiency.

The method of using chemical amplification chemistry has its limitations as well: (a) The method requires application of a polymer/photoresist layer and is not suitable for routine solution reactions since there is no measure provided for separating sites of reaction on a solid surface; (b) in certain circumstances, destructive chemical conditions required for pre- and post-heating and stripping the polymer/photoresist layer cause the decomposition of oligonucleotides on solid surfaces; (c) the entire process is labor intensive and difficult to automate due to the requirement for many cycles (up to 80 cycles if 20-mers are synthesized) of photoresist coating, heating, alignment, light exposure and stripping; (d) the method is not applicable to a broad range of biochemical reactions or biological samples to which chemical amplification reagents are applied since embedding of biological samples in such a polymer/photoresist layer may be prohibitive.

Additional limitations are linked to the use of photomasks in the above two methods: (a) Setup for making a new chip is expensive and time consuming due to a large number of photomasks that have to be made; (b) photolithography equipment is expensive and complicated, and thus, can not be accessed by many interested users; (c) photolithography processes have to be conducted in an expensive cleanroom facility and require trained technical personnel. These limitations undermine the applications of oligonucleotide chips and the development of the various MMA-chips.

Recently a new method for producing biopolymers on biochips and microarrays has been developed. U.S. Pat. No. 6,426,184 describes an apparatus and methods for synthesizing and assays of arrays of biopolymers utilizing PGRs. These PGRs are useful in the synthesis and assays of arrays of biopolymers by virtue of the fact that the precursors of these reagents can be used in conventional synthesis reactions to produce biopolymers with high yield or that the precursors of these reagents can be used in conventional reaction conditions to induce changes in reaction conditions. The production of the PGRs is accomplished by the irradiation of these PGR precursors, which undergo photolytic reaction upon irradiation to produce product or intermediate that can be utilized in synthesis and other chemical reactions.

While not intended for solution reactions, there are ample examples of PGR-P compounds, which are used as polymerization initiators and as reagents used in chemical amplification reactions of photoresists (a polymer matrix). These processes are fundamental to microelectronic fabrication of semiconductor industries. Examples of PGR-P compounds are photogenerated acid precursors (PGA-P) that yield $H^+$ in the form of carboxylic acids, phosphate acids, sulfate acids, and hydrohalogen acids. PGA-P may also be Lewis acids, forming complexes, such as $M_mX_n$ (m and n are number of atoms). Examples of PGR-P compounds also include photogenerated base precursors (PGB-P) that yield a base, such as an amine, a hydroxide or the like, upon irradiation. References for such compounds may be found in Süs et al., *Liebigs Ann. Chem.* 556, 65-84 (1944); Hisashi Sugiyama et al., U.S. Pat. No. 5,158,855 (1997); Cameron et al., J. Am. Chem. Soc. 113, 4303-4313 (1991); Fréchet, *Pure & Appl. Chem.* 64, 1239-1248 (1992); Patchornik et al., J. Am. Chem. Soc. 92, 6333-6335 (1970). PGA-P compounds have been widely used for many years in printing and microelectronics industries as a component in photoresist formulations (Willson, in "Introduction to microlithography", Thompson et al. Eds., Am. Chem. Soc.: Washington D.C., (1994)). A specific example of a PGA-P is triarylsulfonium hexafluoroantimonate derivatives (Dektar et al., *J. Org. Chem.* 53, 1835-1837 (1988); Welsh et al., *J. Org. Chem.* 57, 4179-4184 (1992); DeVoe et al., *Advances in Photochemistry* 17, 313-355 (1992)). This compound belongs to a family of onium salts, which undergo photodecompositions, either directly or sensitized, to form free radical species and finally produce diarylsulfides and $H^+$.

The PGA chemical amplification reaction has recently been modified and applied to an imaging process (acid amplified imaging or AAI, Marshall et al. Science 297, 1516 (2002)). In these solid phase reactions, sensitizer dyes, super sensitizer, iodonium photo-acid generator, and amplifier reagents are present in thin layers with or without the presence of a polymer matrix, such as polystyrene (the binder). It is believed that the AAI reagents are not dissolved in the polymer. Light irradiation activates sensitizers which react with iodonium photo acid generator to produce primary $H^+$. The light activated reaction is accelerated under after heating the thin layers of the AAI reagents to high temperature (140° C.). The system can be stabilized after the AAI reactions by light bleaching the sensitizers, reducing the iodonium salts using hydroquinone reducing agents (fixer), and base neutralizing the acid generated.

The PGA compounds have been shown in solution reactions to be effective for parallel synthesis of microarrays of oligonucleotides and peptides (Gao et al. Nucleic Acids Res. 29, 4744-4750 (2001); Pellois et al., Nature Biotechnol. 20, 922-926 (2002)).

BRIEF SUMMARY OF THE INVENTION

The present invention provides novel compounds and methods of synthesizing novel compounds which can be used for performing chemical and biochemical reactions in solution using irradiation generated products as reagents or co-reagents. The present invention also provides examples for novel uses of these compounds. These compounds when irradiated produce acids, bases or other chemical species that can be used in chemical synthesis or biochemical assays. These novel compounds are of particular use in the parallel synthesis of libraries of bio-organic compounds and biopolymers, such as DNA, RNA, peptides, carbohydrates and combinatorial pharmaceutical organic compounds. These compounds are soluble in solutions of one or more common solvent(s) employed in the chemical reaction, including but not limited to such solvents as $CH_2Cl_2$, $CH_3CN$, toluene, hexane, $CH_3OH$, $H_2O$, DMF ($HC(O)N(CH_3)_2$), and/or an aqueous solution containing at least one added solute, such as NaCl, $MgCl_2$, phosphate salts, etc. In a preferred embodiment of the present invention the compounds can be used as reagent precursors (PGR-P, compounds that form at least one intermediate or product upon irradiation) for chemical synthesis on solid surface, utilizing projected light patterns to initiate reactions. The illuminated PGR-P forms PGR (photogenerated reagent) at illuminated sites; no reaction occurs at dark (i.e., non-illuminated) sites. The PGR-P and PGR of the present invention may be modified by reaction conditions and may undergo further reactions in its confined area as desired. Therefore, in the presence of at least one PGR-P, at least one step of a multi-step reaction at a specific site on the solid surface may be controlled by radiation, such as light, irradiation. Hence, the compounds of the present invention have great potential in the applications of parallel reactions, wherein at each step of the reaction only selected sites in a matrix or array of sites are allowed to react. The compounds of the present invention are of particular use in the methods described in U.S. Pat. No. 6,426,184, which is herein incorporated by reference.

Some of the compounds of the present invention include PGR-P compounds as shown in Table 1. The photoactivable components of these compounds are derived from nitrobenzyl and nitrophenylethyl moieties and undergo photolytic reaction to generate XH. X groups in Table 1 are leaving groups representing piperidine, hydrazine, tetrazole, and other nucleophiles. Different X groups gave different photoreaction yields. For instance, for NBOC (2-nitrobenzyloxycarbonyl) protected carboxyl groups of amino acids, leucine formed in 70% yield versus leu-gly in 84% yield. Piperidine is the deprotecting reagent for the Fmoc-NH-amino acids. Hydrazine deprotects side chain protecting group such as N-levulinyl and N-ivDde (4,4-dimethyl-2,6-dioxocyclohexylidene-)3-methyl-butyl). Tetrazole is a test case of a very weak base, allowing examination of the leaving group effect when compared with the photoreaction properties of the corresponding piperidine and hydrazine derivatives. The substituents, R, exert steric, electronic, and hydrophilic/hydrophobic effects, and thereby cause changes in the chemical and physiochemical properties of the PGR-P compounds. The substituents on the $C_\alpha$ position have been shown to have profound effects on the reactivity and overall efficiency of photolytic reactions by suppressing the formation of secondary photoreaction products. Methyl, phenyl, 2-nitrophenyl, and substituted phenyl or 2-nitrophenyl groups are some examples of $C_\alpha$ substituents. The substituents of the aromatic rings are used to tune the excitation wavelength (Table 2), thermal stability, efficiency of photolytic reactions, solubility, and other properties affecting the reactions. For instance, the methoxy group substituted aromatic systems such as MeNPOC have been used in several photolabile protection systems which shorten the $t_{1/2}$ (half life of the photolytic compound) by 4-fold from that of NVOC (NVOC is α-methyl NBOC); bromo- and nitro-aromatic substitutions will increase the wavelength of the photolytic chromophore group to give quantitative reaction yields via the activation of the 2-nitro group. The trifluoromethyl group is strongly electron withdrawing and also bulky in size. These substituents, when incorporated into the ortho-, para-, or meta-position, will provide PGB-P of vastly different chemical properties.

TABLE 2

UV Absorption of Mono-substitute Benzene.

| No | Substituent | K and B Band Shifted (nm) |
|---|---|---|
| 1 | H | 204 (3.90), 256 (2.30) |
| 2 | OCH3 | 217 (3.81), 269 (3.17) |
| 3 | —Br | 2.10 (3.90), 261 (2.28) |
| 4 | —CN | 224 (4.11), 2.71 (3.00) |
| 5 | —NO₂ | 252 (4.00), 280 (3.00) |

Numbers in parenthases are log(ε), ε is molar extinction coefficient at the indicated wavelength.

The compounds of the present invention include PGR-P compounds as shown in FIGS. 1A and 1B. PGR-Ps are com-

TABLE 1

List of PGR-P Compounds

| Core Structure | Representative/Aromatic Ring Substitution Derivatives | $C_\alpha$-Substitution Derivatives | $2^{nd}$ Generation of Derivatives |
|---|---|---|---|
| NBOC 2-nitrobonzyloxy carbonyl | MeNPOC methylnitropiperonyl carbonyl | DNBOC 2,2'-dinitrodiphenylmethyloxy carbonyl | Substituted-DNBOC |
| NPPOC 2-nitrophenylproxy carbonyl | MNPPOC 2-(3,4-methylonedioxy-6-nitrophenyl)proxy carbonyl | see $C_\alpha$ substitution in NBOC examples | see $C_\alpha$ substitution in NBOC examples |
| NFMOC (2-nitrofluoren-9-yl) methoxycarbonyl | | see $C_\alpha$ substitution in NBOC examples | see $C_\alpha$ substitution in NBOC examples |
| Substitution Examples | Br, NO₂, CF₃, OMe, OCH₂O | | | prised of a photo-activatable group, such as a chromophore, and a photogenerated reagent component. Suitable photoactivatable groups include but are not limited to those listed in FIG. 2. The PGR component may be any chemical entity that can be associated with, preferably covalently linked to the photoactivatable group and released from the photoactivatable group upon irradiation of the PGR-P. Preferred photoactivatable groups of the present invention include UV-Vis absorption moieties, such as a large family of π-conjugated systems, polyaromatic and polyheterocyclic chromophores, aryl and polyaryl sulfonium and iodinium, aryl diazoquinones, sulfonates, arylamines, nitrobenzyl, and aryl or benzocarbonates and carbamates. Many photolabile groups have been used as protecting groups and they are also suitable for use as photo-activable group in PGR-P for generation of PGR (Green and Wuts, Protective groups in organic synthesis. Wiley-Interscience, 1999).

PGR groups of the present invention include common chemical reagents such as amines, alcohols, thiols, and carboxylic acids. Preferred PGR groups of the present invention include piperidine, hydrazine, tetrazole, thiophenol, trifluoroacetic acid (TFA), sulfonic acids, and reagents for phosphorylation.

The preferred PGR-Ps of the present invention include but not limited to 2-(2-nitrophenyl)propoxycarbonyl piperidine (NPPOC-pip), 2-(2-nitrophenyl)propoxycarbonyl hydrazine (NPPOC-Hz), 2-(2-nitrophenyl)propoxycarbonyl tetrazole (NPPOC-tet), 2-(2-nitrophenyl)propoxycarbonyl thiophenol (NNPOC-SPh), 2-(2-nitrophenyl)propyltrifluoroacetate (NPP-TFA), 2-(2-nitrophenyl)propoxyl β-cyanoethyl diisopropyl phosphoramidite (NPPO-ppa), 2-(3,4-methylene-dioxy-6-nitrophenyl)-propoxycarbonyl piperidine, and N-methylsulfonyloxynaphthalimide. The preferred PGR-Ps of the present invention are drawn schematically in FIG. 1A. The PGR-P compounds are not limited to these shown in FIG. 1A. Derivatives of NBOC, MeNPOC, DNBOC (Table 1) and 2-(2-nitrophenyl)propoxysulfonyl (NPPOS) chromophore are also photolabile and their photoreaction products include alcohol compounds ROH, which are potentially useful reagents for organic reactions (Wolfgang Pfleiderer, U.S. Pat. No. 6,153,744).

The applications of the PGR-P compounds of the present invention provide a means for generation of chemical/biochemical reagents that are used in the subsequent chemical and biochemical reactions in selected sites among the many possible sites present. One aspect of the invention is to change solution pH by photogeneration of acids or bases in a controlled fashion. The pH conditions of selected samples can be controlled by the amount of photogenerated acids or bases present. The changes in pH conditions effect chemical or biochemical reactions, such as by activating enzymes and inducing couplings and cross-linking through covalent or non-covalent bond formation between ligand molecules and their corresponding receptors. In other aspects of the present invention, PGRs themselves act as binding molecules that can interact with other molecules in solution. The concentration of PGR for a given PGR-P is determined by light irradiation and by the dose of light irradiation, and thus, the reactivity and the ligand binding affinity and specificity in more than one system can be examined in parallel.

Another important aspect of the compounds of the present invention is parallel synthesis of biopolymers, such as oligonucleotides and peptides, wherein the compounds of the present invention can be used to generate PGRs that are used for selective deprotection or coupling reactions. These reactions permit controlled fabrication of diverse biopolymers on solid surfaces. These molecular microarrays are used in a wide range of fields, such as functional genomics, diagnosis, therapeutics, genetic agriculture, and for detecting and analyzing gene sequences and their interactions with other molecules, such as antibiotics, antitumor agents, oligosaccharides, and proteins.

The use of PGR-P in parallel synthesis of combinatorial library of molecules, especially, of individually addressable microarrays has been demonstrated. According to the articles by Gao et al. (2001, Nucleic Acids Res. 29, 4744-4750) and Pellois et al. (2002, Nature Biotechnol. 20, 922-926), biopolymers are synthesized in high fidelity using PGA. There is a clear need in creating more PGR-P and expanding their applications to a broad range of chemical reactions since the method is particularly suited for miniaturization, automation, and parallelization of combinatorial synthesis. One objective of the present invention is to develop new PGR-P compounds and the applications of PGRs.

BRIEF DESCRIPTION OF THE SEVERAL VIEWS OF THE DRAWING

FIG. 1A shows examples of the preferred PGR-Ps of the present invention.

FIG. 1B shows examples of two-photon sulfonium and iodium compounds.

FIG. 1C shows to examples of other O-nitrophenylethyl compounds.

FIG. 4A shows examples of the reactions for preparation of PGR-Ps based on 2-(2-nitrophenyl)propoxycarbonyl chromophore.

FIG. 5 shows examples of the photolytic reactions of PGR-Ps to form photogenerated reagents (PGRs)

DETAILED DESCRIPTION OF THE INVENTION

The present invention provides compounds that can be utilized in methods for solution based photochemical reactions involving reagents generated by irradiation. A conventional chemical/biochemical reaction occurs between at least one reactant (generically denoted as "A") and at least one reagent (generically denoted as "R") to give at least one product as depicted below:

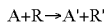

The compounds of the present invention can be utilized in reactions that are controlled by irradiation with light. The compounds of the present invention, PGR-Ps, produce PGRs upon irradiation. The PGR then functions the same as a reagent conventionally used in a chemical reaction, and, thus, the reaction proceeds in an otherwise conventional way. The overall photo-controlled reaction is depicted below.

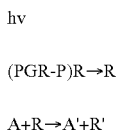

Figure 3:
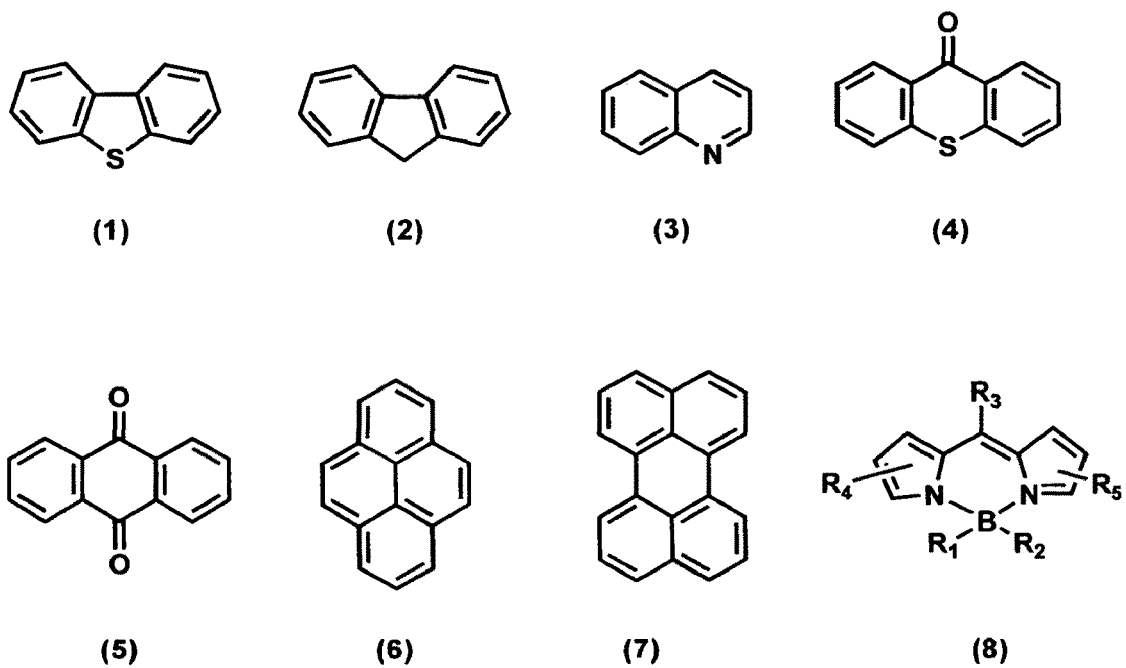
FIG. 3 shows examples of photosensitizers.

The use of PGR in the present invention permits chemical/biochemical reactions under conventional conditions. The occurrence of the reaction is controlled, however, by formation of at least one reagent upon irradiation. In some embodiments, irradiation is from a light source emitting UV and visible light. Heat, IR and X-ray irradiation are also sources of irradiation. A PGR is produced by irradiation of a PGR-P or a PGR-P in combination with a photosensitizer (FIG. 3) which in turn transfers its energy to a PGR-P or affects the excitation energy of PGR-P. The sensitization effect can be enhanced by a supersensitizer which further improves the efficiency of photoreaction conversions. PGR may be an intermediate or a stable compound. The PGR is derived from a portion of the PGR-P molecule which has dissociated from the parent structure or which has been rearranged in structure from the PGR-P. PGR may be an acid, a base, a nucleophile, an electrophile, or other reagents of specific reactivities.

Figure 2:
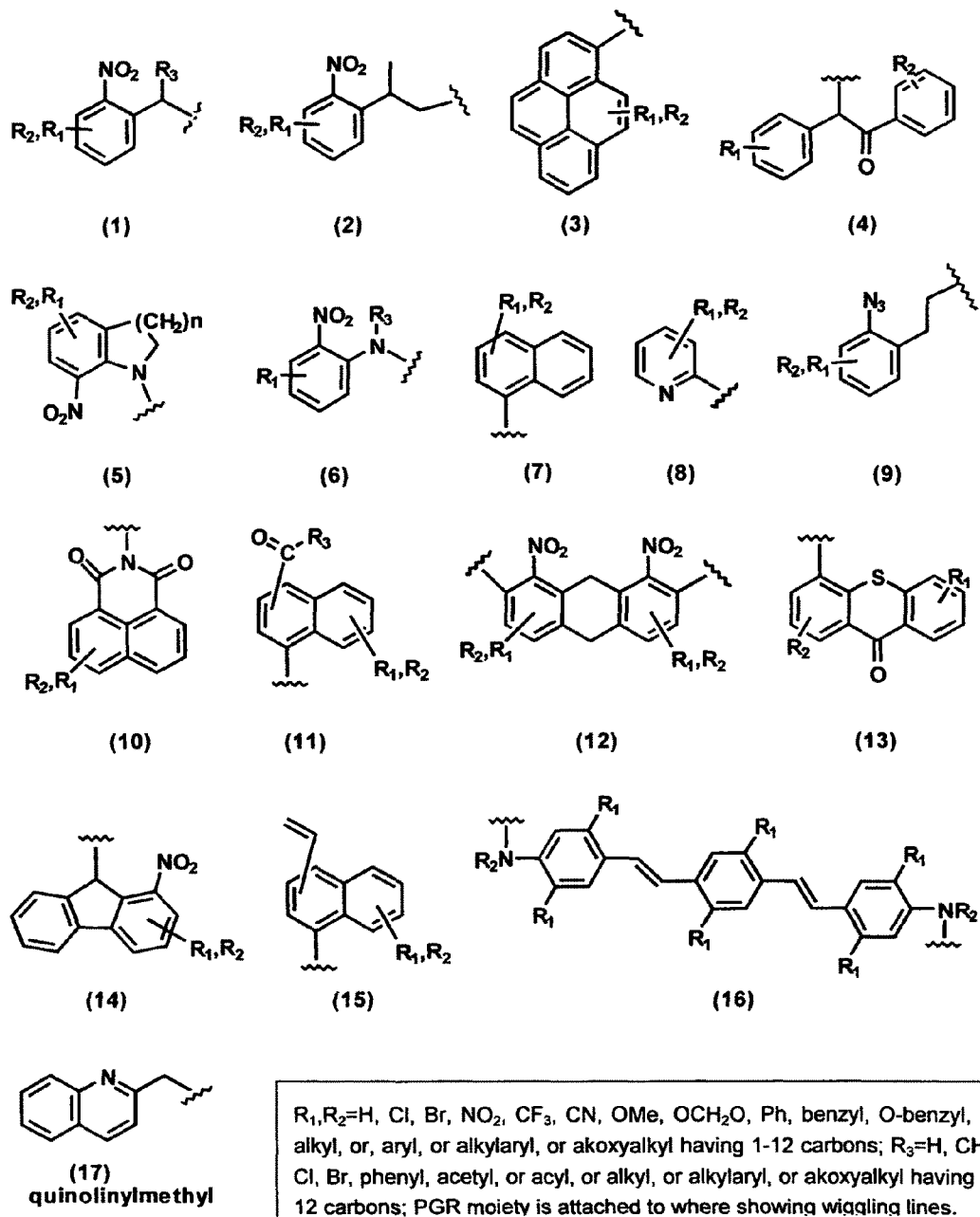
FIG. 2 shows examples of chromophoric photo-active groups as a component of PGR-P

Typically, a PGR-P contains one or more photo-activable chromophoric groups, such as substituted aryls or thiolaryls in onium salt sulfonium hexafluoroantimonate. This family compounds are acid generators and can abstract hydrogen from reaction media to produce strong protic acids. According to the present invention, nitrobenzyl or O-nitrophenylethyl moieties are examples of photo-activable chromophoric groups (FIG. 2). The photo-activable chromophoric groups may be represented by a large family of polyaromatic or polyheterocyclic ring moieties and they undergo reactions via different mechanisms. The photo-activable chromophoric groups useful in the present invention include but are not limited to those shown in FIG. 2. The chromophore portion of the PGR-P serves to absorb radiation, either directly or by energy transfer from a sensitizer. The absorbed energy induces one or more chemical reactions that ultimately result in cleavage of one or more chemical bond in PGR-P, and thus, irradiation leads to the formation of PGR in solution. One embodiment of the invention defines a PGR-P molecule containing one or more chromophoric moieties and one or more chemical moieties, which are precursor of the resulting reagents formed upon irradiation.

The photo-activable group would have the suitable excitation energy and thus at a given wavelength photolytic reaction would occur. It is most desirable that the photolytic reaction is associated with high photochemical quantum yield and produces no harmful side products. The nitrobenzyl derivatives have been used in the last few decades as photo-activable group for protection of functional groups. Examples can be found in the photolabile protection of the amino group of amino acids and hydroxyl group of nucleotides. Recently, photolytic generation of acids from nitrobenzyl derivatives have been used to remove DMT group from nucleotides (Pawel J. Serafinowski and Peter B. Garland PCT WO 03/000644). However, the photolytic reactions of these carbamate and carbonate derivatives in such applications did not provide satisfactory results, which could be due to inefficient photolytic reaction because of low quantum yield of photodeprotection or other unfavorable reaction conditions required by the photolytic reaction. The ortho-nitrophenylethyl carbonyl group was introduced to offer improved stability, several fold enhancement in quantum yield, and shorter deprotection times (Wolfgang Pfleiderer, U.S. Pat. Nos. 5,763,599 and 6,153,744). The ortho-methylenedioxy substitution was introduced to the nitrophenylethyl group in 2-(3,4-methylenedioxy-6-nitrophenyl)-propoxycarbonyl to cause the UV absorption of the molecule red shifted (Berroy et al. Sensors and Actuators B: Chemical, 74, 186 (2001)). In one preferred embodiment of the present invention, useful photoactivable chromophoric group include N—O-substituted 1,8-naphthalimides (NAI) and 1,4,5,8-naphthaldiimides (NDI) derivatives, such as N-sulfonates, N-carbonates, or N-carbamates, which undergo photolytic reaction upon irradiation, resulting in cleavage of the N—O bond to give PGR. The present invention also makes use of, but is not limited to, PGR-P containing conjugated n-molecular structures (FIG. 1). A particular group of these compounds are photogenerated reagents reacting through a two photon photolytic mechanism, based on sulfonium moieties attached to a bis[(diarylamino)styryl]benzene (BDASB) core (Zhou, et al., Science, 296, 1106-1109 (2002); Albota, et al., Science, 281, 1653-1656 (1998)) (FIG. 1B). The photo-activable groups in these molecules are bridged through a D-π-D conjugation system, i.e., BDASB. As a result, the excitation wavelength is shifted to longer than 650 nm and the quantum yield of photochemical reactions is improved by 80% as compared to classic arylsulfonium compounds.

An important aspect of the application of PGRs is the selection of a PGR-P that would produce a PGR at a suitable wavelength. Electromagnetic radiation, in the form of ultraviolet light, visible light, or infrared can be used to generate the reagents. Obviously, the wavelength that maximizes the reaction of the PGR-P to form the reagent will depend on the specific precursor and sensitizer, if any, that are employed, and a wavelength that penetrates the solvent and does not damage other compounds in the reaction solution will be preferred. The duration of irradiation is also dependent on several factors including concentration of the specific precursor employed, the radiance of the light source, and whether a photosensitizer (with or without other co-reagent, such as a stabilizer or H-donor) is present. For organic synthesis, it is desirable to use irradiation at wavelengths longer than 365 nm, since shorter wavelengths may induce undesirable photoreactions among the reactants. The choice of wavelengths is also limited by the compatibility of the photoreaction apparatus. The use of digital photolithography through a micromirror devices to produce PGRs from PGR-Ps is facilitated if the reflected light has wavelength is or above 365 nm. At different wavelengths, there are also various laser light sources and organic light emitting diode devices available as the choices of photoreaction devices using the digital photolithographic approach.

A desirable property of the application of PGRs is the behavior of the PGR induced reactions follows a non-linear correlation of the reaction efficiency with the light strength provided (irradiation time and/or intensity). Examples have been reported in using PGA deprotection of the 5'-DMT group in oligonucleotide synthesis (Gao et al. Nucleic Acids Res. 29, 4744, 2001) or PGA deprotection of the N-t-Boc group in peptide synthesis (Pellois, Ph.D. Dissertation, 2002). This non-linear correlation reduces the side reactions in nonilluminated areas due to the presence of trace PGR generated by stray light or diffusion. In contrast, direct cleavage of a photolabile group such as ((α-methyl-2-nitropiperonyl)-oxy)carbonyl (MeNPOC) often follows a linear correlation (McGall et al. J. Am. Chem. Soc. 119, 5081, 1997), which is more sensitive to the boundary conditions of light irradiation.

In some embodiments of the present invention, PGR-P compounds are used in combination with co-reagents to enhance the reaction. One specific example is the use of photosensitizers and supersensitizer, which are compounds that can lower excitation energies of PGR-P either by direct energy transfer to or through complex formation with PGR-P in the ground or excited state. The sensitizers useful in the present invention include but are not limited to those, the derivatives of thiofluorene, fluorine, quinoline, thioxanthanone, anthraquinone, pyrene, perylene, dipyrromethene boron complex, shown in FIG. 3. Other sensitizers also include benzophenone, acetophenone, benzoinyl C1-C12 alkyl ethers, benzoyl triphenylphosphine oxide, anthracene, $Ru^{2+}$ complexes, or other polyaromatic or polyheterocyclic compounds; optionally substituted on the ring systems with nitro, halogen, alkyl, alkenyl, alkynyl, aryl, alkoxyl, heterocyclic, CN, N(alkyl)2, sulfonyl, alkylsulfonyl, or other aromatic substitution groups. One effect of photosensitizers is to shift the excitation wavelength used in photochemical reaction, and thus, allows the formation of PGR at a wavelength at which the PGR-P alone would not react or would not react efficiently thereby enhancing the efficiency of the formation of photogenerated reagents. Accordingly, in one embodiment, the present invention makes use of, but is not limited to, thioxanthones or perylene, as co-reagents in PGR reactions. The PGR-P photolytic quantum efficiency can be further improved by species that can function as electron transfer intermediates between the primary sensitizer and the PGR-P. In the presence of these co-sensitizers, the generation of PGR proceeds at a faster rate.

Further examples of using co-reagents include the reactions of 2-nitrobenzyl and 2-nitrophenylproxy compounds which are affected by other reagents added to the reaction system. For instance, the side products were significantly suppressed in the reactions of NBOC and NVOC compounds when auxiliary reagents, such as acids mixed with aldehyde reacting reagents (such as hydrazine, hydroxylamine hydrochloride, semicarbazide hydrochloride) were added, and quantitative deprotection yields were obtained for N-protected amino acids (Patchornik et al., J. Am. Chem. Soc. 92, 6333, 1970). A second example is that the cleavage of the 2-nitrophenylproxy group from 5'-O position of nucleotides was inhibited at low pH but enhanced by the presence of co-reagent such as DBU (0.05 M, 1,8-diazabicyclo[5.4.0]undec-7-en) (Walbert et al., Helv. Chim. Acta 84, 1601, 2001). Side reactions due to DBU were not detected. The third example is the usefulness of added acid and base function as buffer to counter the actions of the PGR generated. A desirable condition is that PGR forms in a confined area and there is a high contrast ratio of reacted and unreacted molecules in the peripheral around the reaction site.

In some embodiment of the present invention, the selection of solvent is important. An example is that a PGR-P, such as triarylsulfonium hexafluoroantimonate, undergoes radical reaction to produce a proton, $H^+$. The source of the proton is likely from a H-donor or the surrounding solvent. To facilitate the reaction, a co-reagent called stabilizer of H-donor reagent may be used. The stabilizer or H-donor compounds useful in the present invention include but are not limited to ether solvents, propylene glycol ethers, t-butane, t-butanol, thiols, cyclohexene, chloroform, methylene chloride, and toluene as well as derivatives thereof. One example is to provide at least one reagent to reduce the lifetime of the reactive reaction intermediates, such as a free radical species, generated during irradiation, and to provide a low energy source of hydrogen. The reactions of stabilizer may be uni- or bimolecular or by multistep mechanisms, well-known in photoresist chemistry as acid amplification using acid amplifier reagents.

In some embodiments of the present invention, improved reaction yields and/or suppression of side reactions are achieved by pre-irradiation activation of at least one PGR before mixing with other reactants. Pre-irradiation activation allows time-resolved reaction so that there is sufficient time for potential harmful reaction intermediates, such as free radical species generated during irradiation, to diminish and for products, such as $H^+$, to reach a stable concentration.

In some embodiments of the present invention, the reactions at different reaction sites are modulated by providing irradiation of different strength using a programmable photoreaction optical device, such as Texas Instruments' digital light projector (DLP) or digital micromirror device (DMD). The controlled light irradiation allows control of the reactions to proceed at a desirable rate. Further, the PGR reaction can be controlled or terminated using conventional chemical approaches, such as base neutralization of excess acids or base generated from PGA-P or PGB-P, respectively, and chemically destroy excess PGR-P present in the reaction media to prevent further reactions. Specific examples include using hydroquinone to reduce the PGA-P iodonium salt and using over dose light to bleach the chromophore that is responsible for activating PGR-P.

PGR-P compounds within the scope of the present invention include any compound that produces a product, which potentially is a reagent for a different reaction upon irradiation. Examples of such precursor compounds include but not limited to arylazide derivatives, benzocarbonates or carbamates, dimethoxybeonzoinyl carbonates or carbamates, o-nitrobenzyloxycarbonates or carbamates, nitrobenzenesulphenyl derivatives, and o-nitrobenzyloxyanilines, onium salt of bis[(diarylamino)styryl]benzene, 2-(2-nitrophenyl)propoxycarbonyl or 2-(2-nitrophenyl)propoxyl derivatives, and N-naphthalimide derivatives. Although the examples and discussion herein refer to PGR-Ps that yield a nucleophilic Lewis base, such as an amine, hydrazine, thiol, tetrazole, or the like, upon irradiation, it should be understood that the methods of the invention are applicable to a general scheme which a portion of the molecule is activated upon irradiation and a portion of the molecule is thus chemically converted into a reagent that is required by the subsequent reaction. The examples provided below are exemplification of the specific PGR-P compounds and methods of making these compounds.

According to one embodiment of the present invention PGR-P compounds are derived from 2-nitroethylbenzene derivatives (FIG. 4A), by condensation with formaldehyde in the presence of base to form 2-(2-nitrophenyl)propanols. In an alternate embodiment the reaction can begin with nitrotoluene and formaldehyde, which produce compounds containing 2-nitrophenylethyloxylcarbonyl (NPEOC). The 2-nitrophenylethyloxy and 2-(2-nitrophenyl)propyloxy, or the 2-nitrophenylethyl moieties, are photo-activable chromophores. These compounds are reacted with phosgene or diphosgene to produce the corresponding chloroformates.

Figure 4B:
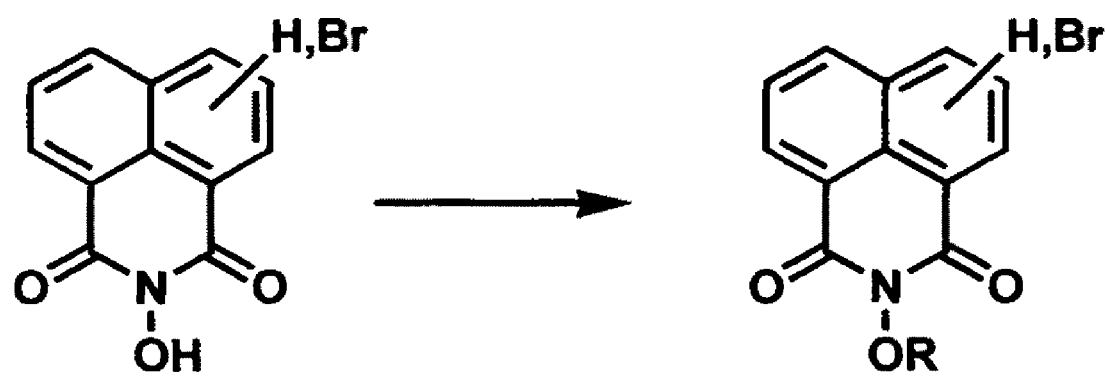
FIG. 4B shows examples of the reactions for preparation of PGR-Ps based on naphthalimide chromophore

Reaction of the chloroformate with a nucleophile or a base, such as piperidine, or hydrazine, or thiophenyl, or tetrazole, readily provides the corresponding PGR-P compounds. One example of PGR-Ps is 2-(2-nitrophenyl)propoxycarbonyl (NPPOC) PGR-P compounds, where NPPOC-pip is a PGB-P (base precursor). 2-(2-nitrophenyl)propanols can directly react as a nucleophile with electron deficient centers, such as a carbonyl or a phosphite (FIG. 4B) to produce the corresponding PGR-P compounds. One example of PGR-P is 2-(2-nitrophenyl)propyltrifluoroacetate (NPP-TFA), where NPP-TFA is a PGA-P (acid precursor). The triphosphite containing 2-(2-nitrophenyl)propyloxyl is a phosphilating agent (FIG. 4B). One application of this compound is to react it with an alcohol and the reaction is followed by oxidation to give a phosphate trimester, which would be converted into a phosphate triester upon light irradiation. Each PGR-P compound is not limited to contain one irradiation or light irradiation activatable center and one PGR moiety. An example is a PGR-P containing two photolytic centers and being able to produce two molecules of photogenerated reagents.

The synthesis of the PGR-P compounds disclosed in the present invention are known to those skilled in the art. N-substituted naphthalimide compounds can be prepared by esterification of N-hydroxynaphthalimide in its salt form with acyl chlorides, acyl anhydrides, sulfonyl chlorides, or sulfonic acid anhydrides. N-carbamates (N—OC(O)NHR) of naphalimides can be prepared by treating N-hydroxysuccinimide with RNCO. 2-(2-nitrophenyl)propoxysulfonyl derivatives of amines or thiols can be prepared by reacting 2-(2-nitrophenyl)propoxysulfonyl chloride with the corresponding nucleophile.

The PGR-P compounds of the present invention become reactive under light irradiation (FIG. 5). The PGR-P compounds are precursors of among others, photogenerated piperidine, or photogenerated trifluoroacetic acid, or photogenerated thiophenol, or photogenerated tetrazole, or photogenerated hydrazine. The reactions occur in solutions of one or more solvents. Such solvents include but are not limited to $CH_2Cl_2$, $CH_3CN$, toluene, hexane, $CH_3OH$, DMF, DMSO, $H_2O$, or mixtures of more than one solvents. The concentration of PGR-P reagent in the solvent can range from 0.1 to 1000 mM, but preferably is in the range between 1 and 200 mM. A range of light sources can be applied to the reaction solution to produce the reagent. Irradiation wavelengths may be from about 254 nm to about 1000 nm, preferably from about 365 nm to about 1000 nm, more preferably from about 405 nm to about 1000 nm.

Figure 6:
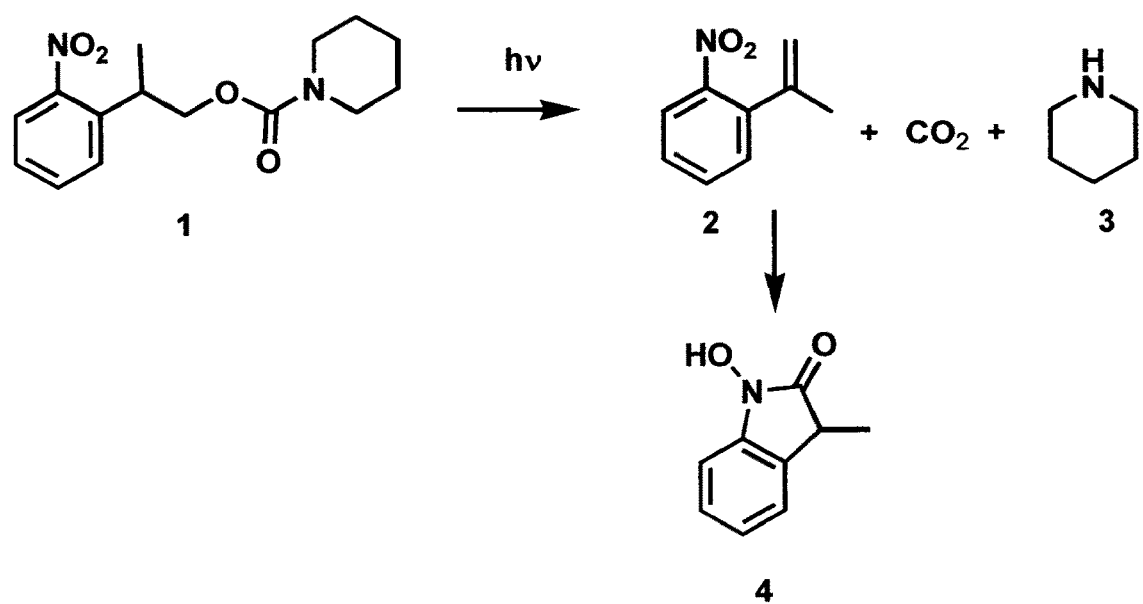
FIG. 6 shows the mechanism of the photolytic reaction of NPPOC-pip.
Figure 7:
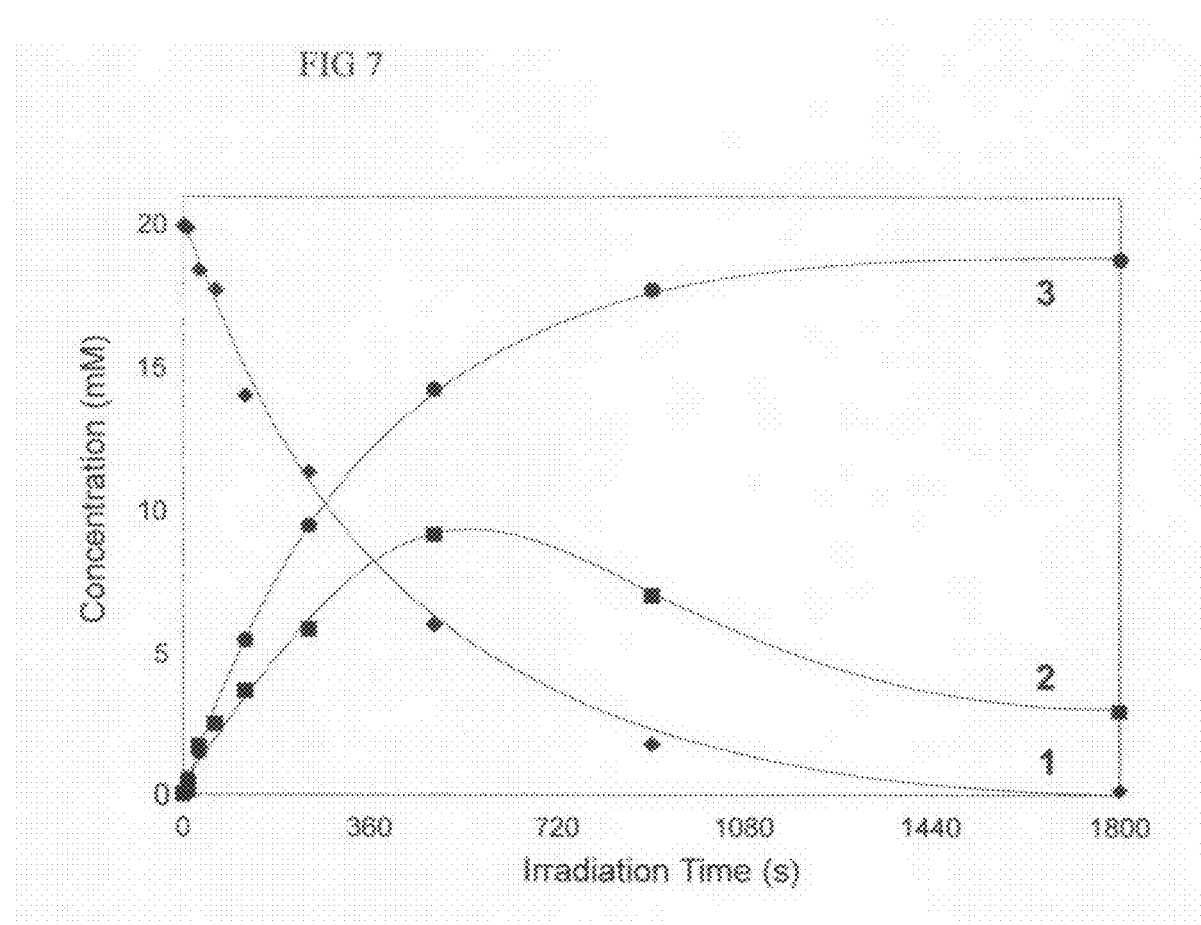
FIG. 7 shows time dependence of the concentration of 2-(2-nitrophenyl)propoxycarbonyl piperidine (NPPOC-pip) (diamond, 1 in FIG. 6), 2-(2-nitrophenyl)propene (square, 2 in FIG. 6), and piperidine (circle, 3 in FIG. 6) upon irradiation in DMF.
Figure 8:
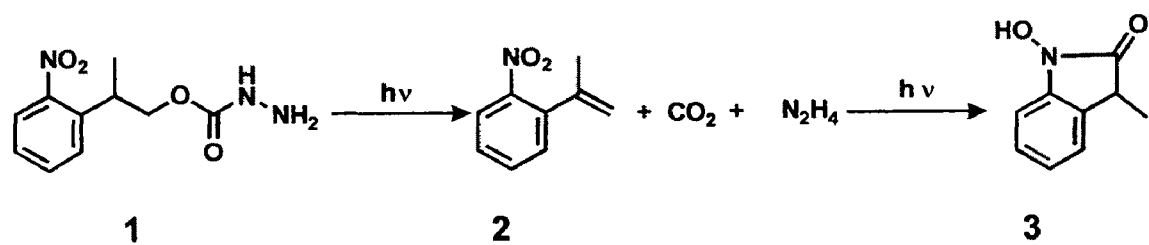
FIG. 8 shows the mechanism of the photolytic reaction of NPPOC-Hz.
Figure 9:
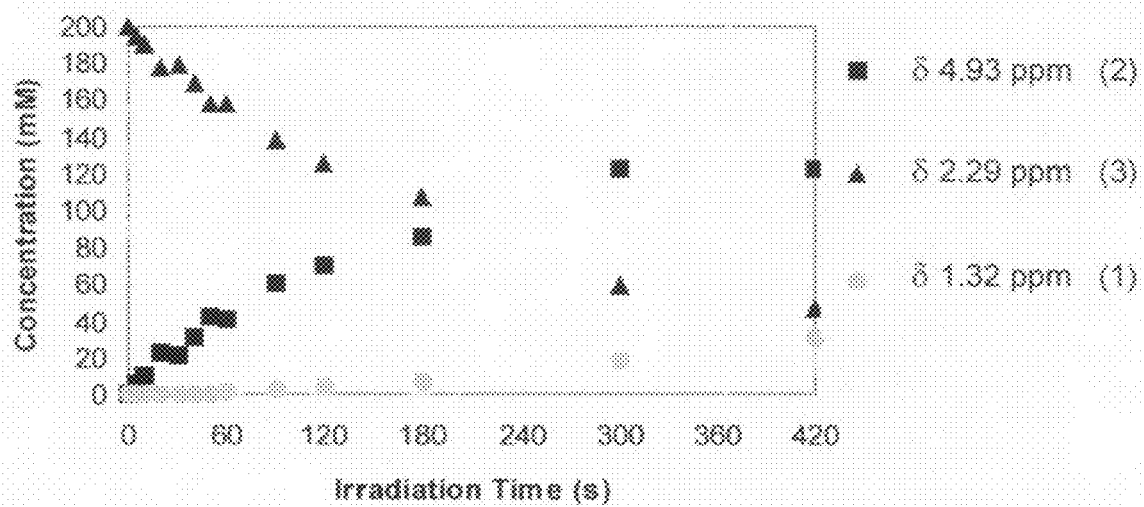
FIG. 9 shows the time dependence of the formation of photogenerated hydrazine. NPPOC-Hz (triangle, 1 in FIG. 8), 2-(2-nitrophenyl)propene (square, 2 in FIG. 8), and 2-methyl-N-hydroxyoxindole (circle, 3 in FIG. 8) upon irradiation in DMF

The photolytic reaction of NPPOC leads to the formation of piperidine, a secondary amine, and 2-(2-nitrophenyl)propene (Wallbert et al. Helvetica Chimica Acta, 84, 1601 (2001), Pellois, J. P. Ph. D. Dissertation, 2002) (FIG. 6), which was detectable by proton NMR based on the presence of two terminal propene protons resonating at 5.19 ppm. Continued light irradiation of the reaction mixture caused 2-(2-nitrophenyl)propene to decompose to give 2-methyl-N-hydroxyoxindole (FIG. 6). This reaction followed a first order kinetics with a rate constant in order of $3.0 \times 10^{-3}$ $s^{-1}$ and the formation of piperidine was quantitative (FIG. 7). In a similar fashion, the photoreaction of NPPOC-hydrazine (NPPOC-Hz) produces hydrazine, a nucleophile, 2-(2-nitrophenyl)propene, and 2-methyl-N-hydroxyoxindole (FIGS. 8 and 9).

Figure 10:
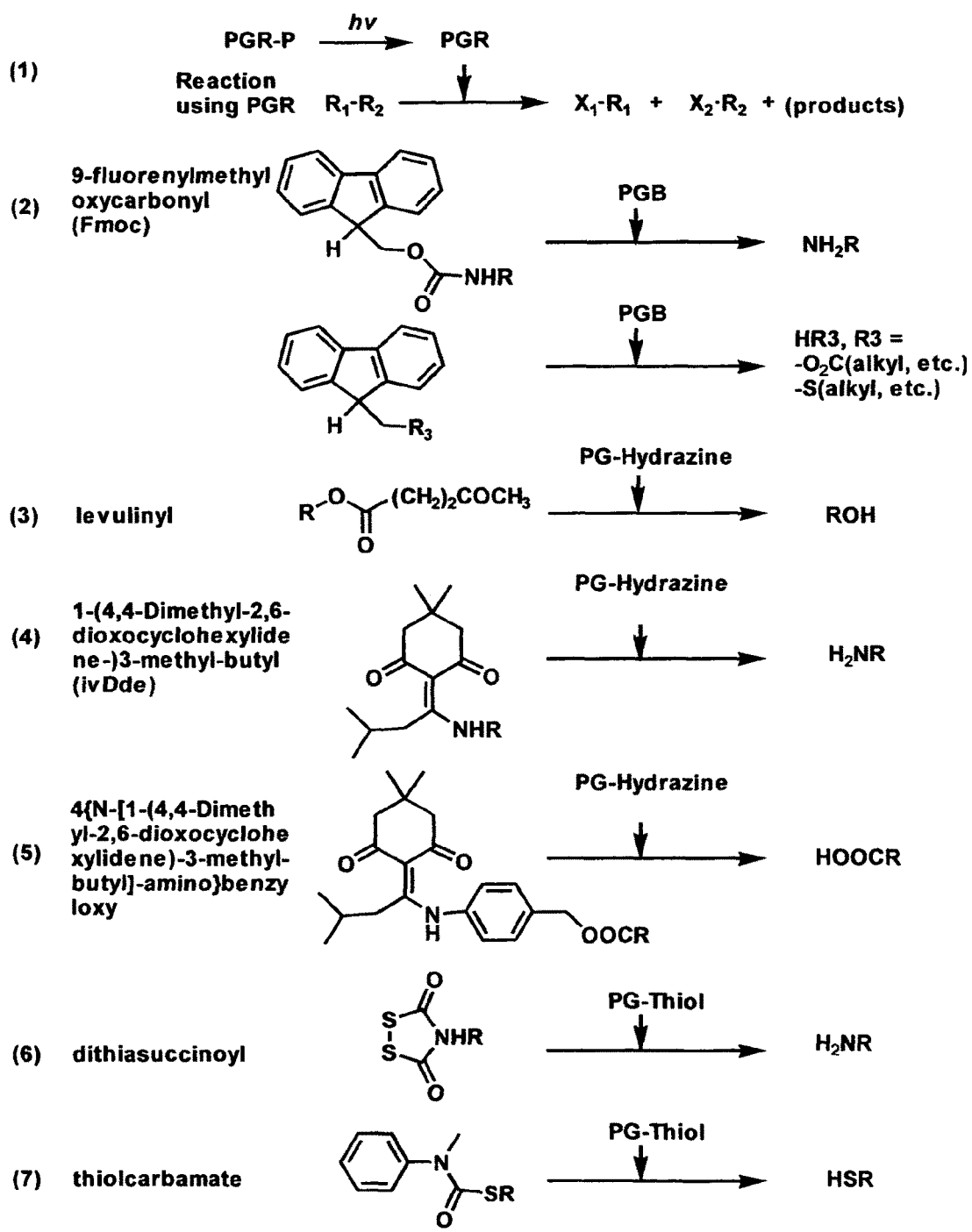
FIG. 10 shows schematics of the formation of the products using various PGR reactions.

In one embodiment of the present invention, the photogenerated piperidine, a PGB, from PGR-P NPPOC-pip is a deprotection reagent for removing 9-fluorenylmethyloxycarbonyl (Fmoc) group from the protected amino group (FIG. 10). Examples of the reactions (FIG. 10) using PGR include deprotection of the levulinyl group from the protected hydroxyl group using photogenerated hydrazine from PGR-P NPPOC-Hz; deprotection of the 1-(4,4-Dimethyl-2,6-dioxocyclohexylidene-)3-methyl-butyl (ivDde) group from protected amino or carboxylic groups using photogenerated hydrazine; deprotection of the dithiasuccinoyl or the thiocarbamate group from the protected thiol or amino groups from photogenerated thiols; deprotection of the acid labile protected hydroxyl or amino groups using photogenerated TFA from NPP-TFA. Photogenerated piperidine or TFA are common reagents for deprotection of amino acids and are wildly used in peptide synthesis. The photogenerated tetrazole is a weak acid and activates the coupling of a phosphoramidite with an alkyl OH group by protonation of the amino group on the phosphite phosphorous. The protonated amino group becomes a good leaving group under nucleophilic attacking conditions, such as coupling of the 5'-OH group with the nucleophosphoramidite monomer. Tetrazole is commonly used as an activating agent in oligonucleotide coupling reactions. These examples demonstrate that photogenerated reagents are convenient ways of control of a wide range of solution reactions by irradiations without significantly changing reaction conditions.

Figure 11:
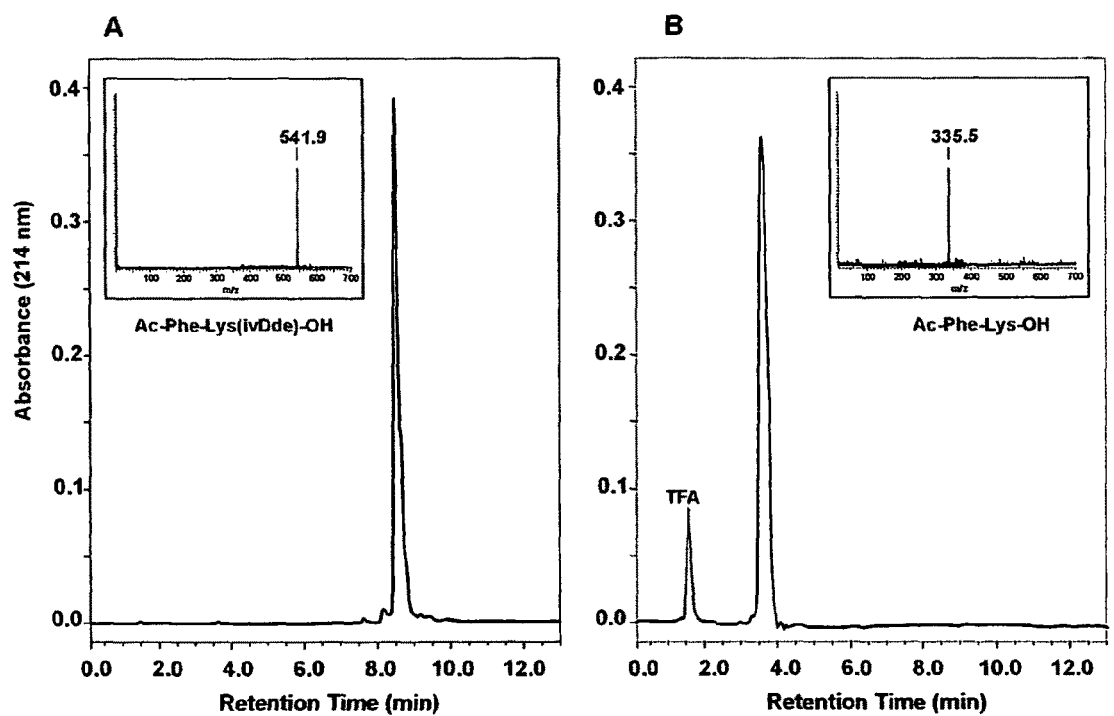
FIG. 11 shows HPLC and Mass characterization for the deprotection reaction using photogenerated hydrazine on the side chain group in Phe-Lys(1-(4,4-dimethyl-2,6-dioxocyclohexylidene-)3-methyl-butyl) (ivDde). Fmoc-Phe-Lys (ivDde) dipeptide was synthesized using photogenerated piperidine.

One embodiment of the present invention illustrates the orthogonal application of the PGR-P compounds, NPPOC-pip and NPPOC-Hz, for peptide synthesis. The reaction began with coupling Fmoc-Lys(ivDde)-OH to solid support, followed by deprotection of Fmoc using the PGB, piperidine, from NPPOC-pip, and coupling to a second amino acid monomer, Fmoc-Phe-OH. The terminal Fmoc of the Phe-Lys (ivDde) dimer on solid support was deprotected using photogenerated piperidine from NPPOC-pip and the deprotected terminal amino group was capped with acetyl (Ac) group to give Ac-Phe-Lys(ivDde) on solid support. NPPOC-Hz was then applied to a portion of the dipeptide and light irradiation produced hydrazine that removed ivDde on the Lys side chain amino group. Finally, dipeptides, Ac-Phe-Lys(ivDde) and Ac-Phe-Lys, were cleaved from solid support. The characterization of the resultant products using HPLC and MALDI mass analysis indicates that the products obtained are as expected (FIG. 11).

Figure 12:
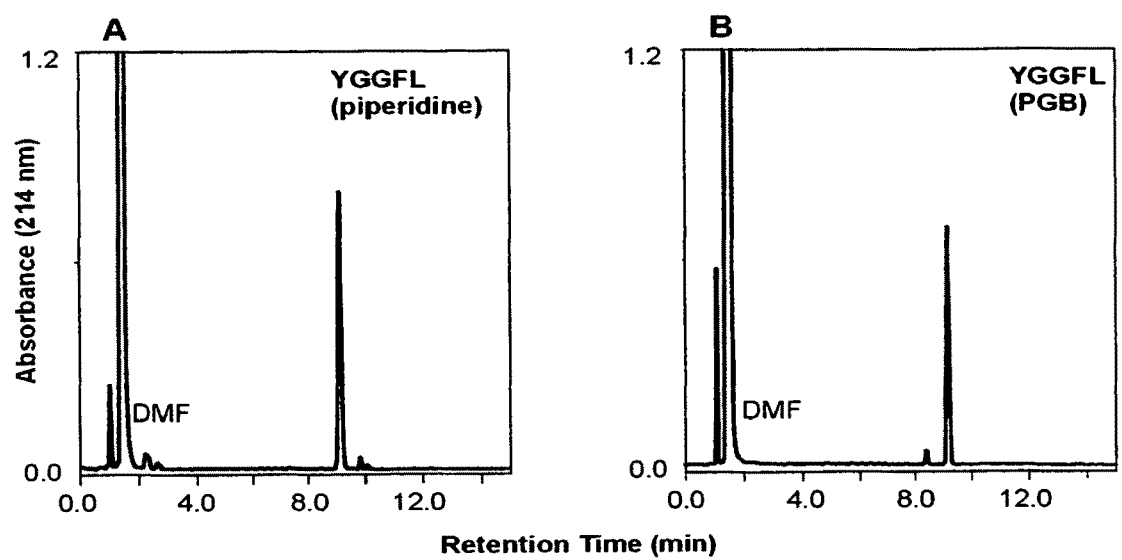
FIG. 12A shows the HPLC profile of pentapeptides Tyr-Gly-Gly-Phe-Leu synthesized using piperidine.
FIG. 12B shows the HPLC profile of pentapeptides Tyr-Gly-Gly-Phe-Leu synthesized using photogenerated piperidine.

One embodiment of the present invention illustrates the application of PGB-P in the preparation of a pentapeptide, leucine enkephalin (SEQ ID 1: Tyr-Gly-Gly-Phe-Leu), using photogenerated piperidine derived from NPPOC-pip as the Fmoc deprotection agent to free the terminal amino group on the growing peptide chain on solid support. The comparison experiment using regular piperidine was run in parallel. The syntheses were performed on resin and all procedures except the deprotection step using NPPOC-pip followed those typical for peptide synthesis. HPLC and MALDI mass analysis demonstrated that the correct sequence was obtained in high quality using PGB-P NPPOC-pip and light irradiation to deprotect the Fmoc amino protecting group (FIG. 12).

The present invention is not limited to the parallel synthesis of individually addressable microarrays of oligonucleotides or peptides. The method is of general use in solid phase synthesis of molecular microarrays where complex synthesis patterns are required at each step of chain extension synthesis. One specific example is synthesis of oligosaccharide arrays containing sequences of diverse carbohydrate units and branched chains. According to the present invention, a PGA-P is applied to a solid surface containing protected carbohydrates. Each carbohydrate molecule contains several reactive OH groups, each of which is protected by a protecting group. Each of these protecting groups requires different deprotection conditions. A predetermined light pattern is then projected onto the substrate surface. At the illuminated sites, acid is produced and the protection groups labile under this particular set of conditions are cleaved. Deprotected OH groups are free to react with an incoming molecule. At the dark sites, no acid is produced and, therefore, the acid labile protecting groups of the carbohydrate molecules remain intact. The substrate surface is then washed and subsequently supplied with a monomer (a carbohydrate or oligosaccharide), which adds only to the deprotected OH under conventional reaction conditions to afford a glycosidic linkage (Wong et al., J. Am. Chem. Soc. 120, 7137-7138 (1998)). These steps are repeated to give oligosaccharides containing various glycosidic linkages at the first deprotected OH position. Next, a PGB-P is applied to the substrate. A second predetermined light pattern is then projected for the second time onto the substrate surface. At the illuminated sites, base is produced and the protection groups labile under this condition are cleaved. Deprotected OH groups of the second batch are free to react with an incoming molecule. At the dark sites, no base is produced and, therefore, the base labile protecting groups of the carbohydrate molecules remain intact. The substrate surface is then washed and subsequently supplied with a second monomer, which adds only to the second deprotected OH of the second time under conventional reaction conditions to afford a glycosidic linkage. These steps are repeated to give oligosaccharides containing various glycosidic linkages at the second deprotected OH position. Branched oligosaccharides are formed. In continued synthesis, various PGR are used to achieve selective deprotection of the OH protecting groups until desired oligosaccharide microarrays are synthesized.

The present invention is not limited to the parallel synthesis of individually addressable microarrays of oligonucleotides, peptides, or oligosaccharides. In one embodiment of the present invention, the selective deprotection of the amino groups of the growing peptide chain using PGR at selected locations is following by coupling of nucleotide phosphoramidite. The microarray thus synthesized contains peptides and peptide-oligonucleotide conjugates, which are library molecules useful for many biochemical and biomedical assays. The syntheses of molecular microarrays containing conjugates of oligonucleotide-peptide, oligonucleotide-carbohydrate, peptide-carbohydrate are possible to those skilled in the art.

The present invention is not limited to the parallel synthesis of individually addressable microarrays of oligonucleotides, peptides, oligosaccharides, or their conjugates. In one embodiment of the present invention, the reaction surface is derivatized with organic scaffold molecules, which share common structures but each of which contain several protected functional groups. Using a similar orthogonal, stepwise deprotection strategy, different substituent groups are attached to the scaffold molecules through multi-step reactions. These reactions result in molecular libraries of combinatorial organic molecules, which are located in a known address in the microarray and thus can be quickly assayed. Examples of useful organic libraries include purine derivatives as kinase inhibitors and triazine derivatives as factor Xa inhibitors.

The present invention enables use of photogenerated reagents in more cases than just deprotection reactions to achieve selective reaction in accordance with a predetermined pattern without changing the course of well-developed conventional chemistry. Furthermore, the present invention is not limited to deprotection reactions, photogenerated reactive compounds, such as alcohols (ROH, R=alkyl, aryl and their substituted derivatives), can be used as reagents for a variety of chemical conversions, such as esterification, nucleophilic substitution and elimination reactions. These reactions are important steps for fabrication of molecular microarrays containing a variety of organic and bioorganic molecules.

The applications of PGR-P in chemical reactions rely on efficient generation and availability of the reagent required for intended reactions, the compatibility of the photo-products forms with the on-going reactions, and the availability of the PGR-P compounds. One of skill in the art can apply the PGR reactions described herein to other types of chemical conversions using suitable PGR-P and reaction conditions. As important considerations as in conventional chemical reactions, the chemical properties of the PGR, such as chemical reactivity, solubility, acidity, basicity, nucleophilicity, polarity, and molecular size, are also determination factors for the success of chemical reactions using PGR reagents.

EXAMPLES

Example I

Synthesis of 2-(2-nitrophenyl)propoxycarbonyl piperidine (NPPOC-pip)

2-(2-nitrophenyl)propoxyl chloroformate (FIG. 4A, eq. 1). 1-Ethyl-2-nitrobenzene (13.5 mL, 100 mmol) was dissolved in dimethylsulfoxide (100 mL). Paraformaldehyde (4.50 g, 150 mmol) and KOtBu (2.81 g, 25 mmol) in t-butyl alcohol (30 mL) were added and the mixture was stirred at room temperature for 3 h. The solution was washed with a molar solution of HCl (25 mL), followed by brine (3×100 mL). All the aqueous layers were combined and extracted with ethyl acetate (3×100 mL). The organic portion was dried (MgSO$_4$), filtered and the solvent was removed in vacuo. The crude product was purified on a silica gel column. Elution of the column with 20-30% ethyl acetate in hexanes gave 16.12 g (89 mmol, 89% yield) of 2-(2-nitrophenyl)propanol. $^1$H-NMR (600 MHz, DMSO-d$_6$): δ 7.75 (d, J=8.10 Hz, 1H, Ar—H), 7.63 (t, J=7.62 Hz, 1H, Ar—H), 7.58 (d, J=7.80 Hz, 1H, Ar—H), 7.42 (t, J=7.50, 1H, Ar—H), 4.73 (t, J=5.30 Hz, 1H, OH), 3.50 (m, 2H, CH$_2$), 3.19 (m, 1H, CH), 1.21 (d, J=6.90 Hz, 3H, CH$_3$). TLC: 20% ethyl acetate in hexane, Rf=0.3.

A solution of 2-(2-nitrophenyl)propanol (16.12 g, 89 mmol) and triethylamine (12.4 mL, 89 mmol) in anhydrous tetrahydrofuran (THF) (96 mL) was added to a cold solution (0° C.) of diphosgene (10.7 mL, 89 mmol) in anhydrous THF (40 mL) over a period of 15 min with stirring and under nitrogen. After 30 min the cooling bath was removed and stirring was continued at room temperature for 3 h. The mixture was filtered and washed with THF. The solvent was removed in vacuo to give 28.20 g of 2-(2-nitrophenyl)propyl chloroformate as light brown oil that was directly used for the next reaction step. TLC: 20% ethyl acetate in hexanes, Rf=0.66.

2-(2-nitrophenyl)propoxycarbonyl piperidine (FIG. 4A, eq. 3, R=101). A solution of piperidine (22.8 mL, 230 mmol) in anhydrous THF (50 mL) was added dropwise to a solution of 2-(2-nitrophenyl)propyl chloroformate (28.20 g) in anhydrous THF (100 mL). The reaction mixture was then brought to reflux for 3 h and stirred at room temperature overnight. The solvent was evaporated to afford light brown oil. The mixture was diluted with ether (100 mL) and water (100 mL) was added. The organic phase was separated and the aqueous phase was re-extracted with ether (3×50 mL). The organic extracts were combined and dried over MgSO$_4$, filtered, and the solvent was removed in vacuo. The residue was purified on a silica gel column. Elution of the column with 20% ethyl acetate in hexanes gave 16.54 g (56.6 mmol, 63.6% yield, 56.6% total yield) of 2-(2-nitrophenyl)propoxycarbonyl piperidine. $^1$H-NMR (600 MHz, DMF-d$_7$): δ 7.88 (d, J=8.1 Hz, 1H, Ar—H), 7.74 (m, 2H, Ar—H), 7.53 (t, J=7.1 Hz, 1H, Ar—H), 4.23 (m, 2H, CH$_2$), 3.54 (m, 1H, CH), 3.24 (m, 4H, CH$_2$), 1.50 (m, 2H, CH$_2$), 1.35 (m, 7H, CH$_2$ and CH$_3$). $^{13}$C-NMR (150 MHz, DMF-d$_7$): δ 155.09 (OCOR), 151.50 (C ipso to NO$_2$), 137.90 (C ipso to CH(CH$_3$)CH$_2$OCOR), 133.49 (C para to NO$_2$), 129.31 (C para to CH(CH$_3$)CH$_2$OCOR), 128.44 (C ortho to CH(CH$_3$)CH$_2$OCOR), 124.35 (C ortho to NO$_2$), 69.45 (CH$_2$OCOR), 45.08 (Cα to ring N), 34.26 (CH), 26.08 (Cβ to ring N), 24.69 (Cγ to ring N), 17.91 (CH$_3$). TLC: 20% ethyl acetate in hexanes, $R_f$=0.4. Mass analysis (MALDI-TOF): calculated for C$_{15}$H$_{21}$N$_2$O$_4$ 293.34, found 293.24.

Example II 2-(2-nitrophenyl)propoxycarbonyl hydrazine (FIG. 4A, eq. 3, R=102) (NPPOC-Hz). A solution of 2-(2-nitrophenyl) propyl chloroformate (6.0 g, 24.6 mmol) in methylene chloride (20 mL) was added dropwise to a solution of hydrazine (3.0 mL, 98 mmol) in methylene chloride (50 mL) over a period of 30 min. The reaction mixture was stirred at room temperature for an additional 15 min. The solvent was evaporated to afford light brown oil. The residue was purified on a silica gel column. Elution of the column with 20% ethyl acetate in hexanes gave 3.35 g (14 mmol, 57% yield) of 2-(2-nitrophenyl)propoxycarbonyl hydrazine. $^1$H-NMR (600 MHz, DMSO-d$_6$): δ 8.10 (s, 2H, CONH), 7.82 (d, J=7.5 Hz, 1H, Ar—H), 7.67 (m, 2H, Ar—H), 7.47 (m, 1H, Ar—H), 4.15 (d, J=7.2 Hz, 2H, CH$_2$), 3.9 (s, 2H, NH$_2$), 3.39 (m, 1H, CH), 1.25 (d, J=6.9 Hz, 3H, CH$_3$). $^{13}$C-NMR (150 MHz, DMSO-d$_6$): δ 157.99 (OCOR), 150.00 (C ipso to NO$_2$), 136.72 (C ipso to CH(CH$_3$)CH$_2$OCOR), 132.86 (C para to NO$_2$), 128.55 (C para to CH(CH$_3$)CH$_2$OCOR), 127.69 (C ortho to CH(CH$_3$)CH$_2$OCOR), 123.68 (C ortho to NO$_2$), 67.49 (CH$_2$OCOR), 33.36 (CH), 17.93 (CH$_3$). Mass analysis (MALDI-TOF): calculated for C$_{10}$H$_{13}$N$_3$O$_4$ 239.23, found 239.20 (C$_{10}$H$_{13}$N$_3$O$_4$Na 262.18 is the major peak). TLC: 5% methanol in chloroform, $R_f$=0.5.

Example III

Di-(2-(2-nitrophenyl)propoxycarbonyl)hydrazine. A solution of hydrazine (0.32 mL, 10.25 mmol) in DCM (20 mL) was added dropwise to a solution of 2-(2-nitrophenyl)propyl chloroformate (5.0 g, 20 mmol) in methylene chloride (25 mL) over a period of 30 min. The reaction mixture was stirred at room temperature for an additional 15 min. The solvent was evaporated and the residue was purified on a silica gel column. Elution of the column with 20% ethyl acetate in hexanes gave 1.46 g (3.26 mmol, 32% yield) of di-(2-(2-nitrophenyl) propoxycarbonyl)hydrazine. $^1$H-NMR (300 MHz, DMSO-d$_6$): δ 9.06-8.73 (d, 1H, CONH), 7.84 (d, J=7.8 Hz, 1H, Ar—H), 7.63 (m, 2H, Ar—H), 7.48 (m, 1H, Ar—H), 4.20 (m, 2H, CH$_2$), 3.39 (m, 1H, CH), 1.26 (d, J=6.9 Hz, 3H, CH$_3$). $^{13}$C-NMR (75 MHz, DMSO-d$_6$): δ 156.19 (OCOR), 149.85 (C ipso to NO$_2$), 136.53 (C ipso to CH(CH$_3$)CH$_2$OCOR), 132.91 (C para to NO$_2$), 128.52 (C para to CH(CH$_3$) CH$_2$OCOR), 127.76 (C ortho to CH(CH$_3$)CH$_2$OCOR), 123.77 (C ortho to NO$_2$), 67.86 (CH$_2$OCOR), 33.30 (CH), 17.99 (CH$_3$). Mass analysis (MALDI-TOF): calculated for C$_{20}$H$_{22}$N$_4$O$_8$ 446.42, found 446.24 (C$_{20}$H$_{22}$N$_4$O$_8$Na 469.38 is the major peak). TLC: 5% methanol in chloroform, $R_f$=0.7.

Example IV 2-(2-nitrophenyl)propoxycarbonyl thiophenol (FIG. 4A, eq. 3, R=104). A solution of thiophenol (2.5 mL, 24.6 mmol) in anhydrous THF (10 mL) was added dropwise to a solution of 2 (4 g) in anhydrous THF (20 mL). The reaction mixture was then brought to reflux for 6 h and stirred at room temperature overnight. The solvent was evaporated to afford light yellow oil. The mixture was diluted with ether (20 mL) and water (20 mL) was added. The organic phase was separated and the aqueous phase was re-extracted with ether (3×10 mL). The organic extracts were combined and dried over MgSO$_4$, filtered, and the solvent was removed in vacuo. The residue was purified on a silica gel column. Elution of the column with 20% ethyl acetate in hexanes gave 3.2 g (10.3 mmol, 42.0% yield,) of 2-(2-nitrophenyl)propoxycarbonyl thiophenol. $^1$H-NMR (300 MHz, CDCl$_3$): δ 7.80 (d, J=6.9 Hz, 1H, Ar—H), 7.47 (m, 8H, Ar—H), 4.41 (d, J=6.0 Hz, 2H, CH$_2$), 3.72 (m, 1H, CH), 1.35 (d, 6.3 Hz, 3H, CH$_3$). $^{13}$C-NMR (75 MHz, CDCl$_3$): δ 169.71 (OCOR), 150.27 (C ipso to NO$_2$), 136.88 (C ipso to CH(CH$_3$)CH$_2$OCOR), 135.04 (C para to NO$_2$), 132.88, 129.80, 129.33, 128.54, 128.18, 127.63, 124.49, 71.25 (CH$_2$OCOR), 33.42 (CH), 17.72 (CH$_3$).

Example V

Photometric Analysis of the Photoreaction of NPPOC-Pip

This experiment demonstrates efficient generation of the base piperidine upon light irradiation of a PGB-P as monitored by increased UV absorbance value of the dye and pH indicator fluorescein as a function of light irradiation time.

Fluorescein was purified in the lactone form as follows: the dye was dissolved in dilute aqueous NaOH, filtered, precipitated by adding dilute HCl, and dried under vacuum overnight. A stock solution of fluorescein (12 µM) in distilled DMF was prepared. To calibrate the absorption of fluorescein, different amounts of piperidine in DMF were added to 0.5 mL of the fluorescein solution in a 1 cm quartz cuvette. After mixing, the UV-Vis absorption spectra of the mixture were recorded. The increase of absorbance at 521 nm was correlated to the amount of piperidine added (after volume correction calculations). 2-(2-nitrophenyl)propoxycarbonyl piperidine (5.84 mg, 20 mM) in 1 mL DMF was prepared and irradiated at 365 nm using a collimated light source (20 mW, Oriel, Stanford, Calif.). Aliquots (10 to 20 µL) of the irradiated sample were added to fresh fluorescein solution (0.5 mL, 12 µM) and to DMF (0.5 mL). Absorbance at 521 nm was recorded (aliquots of the non-irradiated photogenerated base mixture in DMF was used to verify that absorbance of the photoproducts at 521 nm was negligible) and correlated to the amount of piperidine produced upon irradiation. Measurements for calibration and irradiated samples were carried out the same day and repeated three times.

In FIG. 7 (curve 3), the estimated concentration of piperidine produced upon increasing irradiation time is plotted. The formation of piperidine under the conditions used follows a first order kinetics relationship and the apparent rate constant for formation of piperidine derived is $3.0 \times 10^{-3} \pm 0.1$ s$^{-1}$.

Example VI

NMR Experiments of the Photoreaction of NPPOC-Hz. A Bruker Avance 600 MHz NMR instrument was used for data acquisition. Samples of 2-(2-nitrophenyl)propoxycarbonyl hydrazine (23.9 mg, 100 µmol, 200 mM) (FIG. 1A) were prepared in 0.5 mL of N,N-dimethylformamide-d$_7$, transferred into 5 mm NMR tubes, and protected from light. Typically, at the beginning of an experiment, a sample was placed in the detection probe in the NMR instrument and a spectrum was immediately recorded. The sample was removed from the instrument and irradiated carried directly with a light beam (350-450 nm) covering the entire surface of the sample for a fixed duration of time. After irradiation, the sample was quickly placed into the NMR detection probe again and one-dimensional proton NMR spectrum was immediately recorded within 1 min following the end of irradiation. A single scan was recorded with a time domain data size of 16,384 points and a spectral width of 5495 Hz. Chemical shifts were from the calibration of DMF-$d_7$ for the residual HC peak at 8.01 ppm ($^1$H). The rest of the NMR peaks were integrated used 8.01 ppm peak as the reference. The following set of peaks were assigned to 2-(2-nitrophenyl)propene (FIGS. 6, 2), appearing progressively upon light irradiation. $^1$H-NMR (300 MHz, DMF-d7): δ 7.95 (d, J=7.10 Hz, 1H, Ar—H), 7.72 (t, J=7.45 Hz, 1H, Ar—H), 7.59 (t, J=7.80 Hz, 1H, Ar—H), 7.50 (d, J=7.81 Hz, 1H, Ar—H), 5.20 (s, 1H, CH), 4.92 (s, 1H, CH), 2.08 (s, 3H, CH3). The appearance of 2-methyl N-hydroxyoxindole (FIGS. 6, 4) was discernible. The markers used for the detection were δ 1.32 ($CH_3$) for 2-(2-nitrophenyl)propoxycarbonyl hydrazine δ 4.92 (terminal ethylene $CH_2$) for 2-(2-nitrophenyl)propene, and δ 2.29 ($CH_3$) for 2-methyl N-hydroxyoxindole. These results were plotted in FIG. 9, suggesting NPPOC-Hz photolysis undergoes a mechanism similar to that of NPPOC-pip with intramolecular hydrogen abstraction, followed by β-elimination and decarboxylation to give hydrazine and 2-(2-nitrophenyl)propene.

Example VII

Stability Test of Fmoc and ivDde Protected Amino Acid

Light irradiation without the presence of PGR-P. A sample of Fmoc-Lys(ivDde)-OH (5.74 mg, 10 µmol) in 0.5 mL DMF-$d_7$ was placed in the reaction vessel usually used for peptide synthesis using PGR deprotection. The sample was then irradiated for 30 min (350-450 nm, 80 mW/cm$^2$ measured at 400 nm, or 365 nm, 20 mW/cm$^2$ measured at 365 nm). The solution was transferred to a NMR tube and analyzed. HPLC, mass NMR analysis showed that the recovered compound was identical to the starting material Fmoc-Lys(ivDde)-OH. HPLC: 1 peak Rt=13.06 min. $^1$H NMR (300 MHz, DMF-d7): δ 13.81 (s, 1H, εNH), (7.94-7.32 (m, 8H, Fmoc ArH), 7.63 (d, 1H, αNH), 4.28 (m, 3H, Lys αCH, Fmoc $CH_2$), 4.18 (m, 1H, Fmoc CH), 3.57 (q, $J_1$=5.4 Hz, $J_2$=6.6 Hz, 2H, εCH$_2$), 3.07 (m, 2H, ivDde CH$_2$CH), 2.29 (s, 4H, ivDde CH$_2$), 1.92 (m, 2H, βCH$_2$), 1.83 (m, 1H, ivDde CH), 1.71 (m, 2H, δCH$_2$), 1.62 (m, 2H, γCH$_2$), 0.96-0.94 (s, 12H, CH$_3$). Mass analysis (MALDI-TOF): calculated for Fmoc-Lys (ivDde)-OH 574.70, found 575.00.

NPPOC-Hz mixing with Lys(ivDde) but without light irradiation. To Fmoc-Lys(ivDde)-OH (28.7 mg, 50 µmol) was added 2-(2-nitrophenyl)propoxycarbonyl hydrazine (35.8 mg, 150 µmol) in 0.5 mL DMF-$d_7$. The mixture was agitated for 3 h in dark. The $^1$H and $^{13}$C NMR spectra of the reaction solution recorded before and after the treatment did not show any change in chemical shifts.

NPPOC-Hz mixing with Lys(ivDde)-resin but without light irradiation. To Fmoc-Lys(ivDde)-resin (10 mg) was added 2-(2-nitrophenyl)propoxycarbonyl hydrazine (95.6 mg, 400 µmol, 200 mM) in 2 mL of DMF. The mixture was shaken for 3 h in a dark room. The resin was washed with DMF (5×1 mL), 10% DIPEA in DMF (5×1 mL), and DCM (5×1 mL). The peptide was then cleaved from the resin. HPLC: 1 peak Rt=12.98 min (reference compound, Rt=13.06 min), NMR identical to Fmoc-Lys(ivDde). Mass analysis (MALDI-TOF): calculated for Fmoc-Lys(ivDde)-OH 574.70, found 575.07.

NPPOC-Hz mixing with Phe-Lys(ivDde) but without light irradiation. To Ac-Phe-Lys(ivDde)-resin (10 mg) was added 2-(2-nitrophenyl)propoxycarbonyl hydrazine (95.6 mg, 400 µmol, 200 mM) in 2 mL DMF. The mixture was shaken for 3 h in a dark room. The resin was washed with DMF (5×1 mL), 10% DIPEA in DMF (5×1 mL), and DCM (5×1 mL). The peptide was then cleaved from the resin as described. HPLC, mass NMR analysis showed that the recovered compound was identical to Ac-Phe-Lys(ivDde)-OH. HPLC: 1 peak Rt=8.53 min, identical to the reference Ac-Phe-Lys(ivDde)-OH. NMR identical to Ac-Phe-Lys(ivDde)-OH. Mass analysis (MALDI-TOF): calculated for Ac-Phe-Lys(ivDde)-OH 541.7, found 541.6.

Example VIII

Deprotection of Amino Acids Using PGB

To Fmoc-Tyr(tBu)-Wang resin (5 mg, 5 µmol) was added 2-(2-nitrophenyl)propoxycarbonyl piperidine in 2 mL DMF (58.4 mg, 200 µmol, 100 mM). In one reaction set, the solution was left in the dark for at least 30 min and washed with DMF. In a second set, the resin was washed with DMF, immersed in 2 mL DMF, and UV irradiated (365 nm) for 15 min. Both reaction products gave a negative ninhydrin test. For both reactions, after washing with DMF and DCM, the resin was treated with TFA/water (95:5) for 3 h for deprotection of tBu and the molecule was cleaved from resin. The products were analyzed by HPLC.

In a third set, the reaction solution was UV illuminated (365 nm) for 15 min. The amino acid on resin was washed with DMF, dioxane/water (2:1), DMF, and DCM. Positive ninhydrin test was observed. The resin was then treated with Fmoc-Leu-OH (14.1 mg, 40 µmol) using coupling reagents DIC (6.2 µL, 40 µmol) and HOBt (6.1 mg, 40 µmol) in DMF/DCM for 1 h or repeated until a negative ninhydrin test was observed. After washing with DMF and DCM, the resin was treated with TFA/water (95:5) for 3 h for deprotection of tBu and the peptide was cleaved from resin. The product was examined using HPLC.

HPLC elution solvents were water and acetonitrile containing 0.1% and 0.08% TFA, respectively. The gradients used were 15 to 80% of water in acetonitrile in 13 min. The Fmoc-Tyr-OH and Fmoc-Leu-Tyr-OH synthesized on resin using conventional piperidine deprotection (20% in DMF, 1×2 min, 1×15 min) were used as the reference compounds. HPLC retention times were 9.2 min for Fmoc-Tyr(tBu)-OH, 7.7 min for Fmoc-Leu-Tyr-OH, and 6.7 min for Fmoc-Tyr-OH. The correct identity of the PGB deprotection products was also confirmed by co-injection of an equal amount of the product and the reference compound Fmoc-Leu-Tyr-OH, confirming identical HPLC retention times and UV absorption profile. Upon light irradiation, the observed deprotection efficiency (% of HPLC peak integration) is 98%. In the absence of light, no deprotection was detected.

Example IX

Peptide Synthesis Using NPPOC-Pip and NPPOC-Hz

Fmoc-Lys(ivDde)-resin. Fmoc-Lys(ivDde)-OH (29 mg, 50 µmol) was attached to 2-chlorotrityl chloride on Wang resin (Novabiochem, La Jolla, Calif.) (50 mg, 41 µmol) by mixing the amino acid, the resin, and diisopropylamine (DIPEA, 35 µL, 200 µmol) and stirring for 30 min. The resin was then washed with DCM and treated with CH$_3$OH/DCM/DIPEA (8:1:1) for 10 min to cap the unreacted trityl chloride sites.

Ac-Phe-Lys(ivDde)-resin. To the Fmoc-Lys(ivDde)-resin (10 mg, ~8 µmol) was added 2-(2-nitrophenyl)propoxycarbonyl piperidine (58.4 mg, 200 µmol, 100 mM) in 2 mL DMF. A standard TLC visualization UV lamp (350-450 nm) was pointed towards the reaction vessel and turned on for 10 min. The resin was then extensively washed with DMF, dioxane/water (2:1), DMF, and DCM. After washing, a ninhydrin test was performed to confirm the presence of free amino groups.

To the deprotected Lys-resin sample was added Fmoc-Phe (8.8 mg, 33.2 µmol) in DCM/DMF and 1,3-diisopropylcarbodiimide (DIC) (3 µL, 20 µmol). The coupling reaction was continued for 2 h and ninhydrin tests gave negative amino group readings. The Fmoc-Phe-Lys(ivDde) on resin was then treated with photogenerated piperidine as described above. Upon completion of the reaction, the resin was washed with DCM/DMF. Capping of the NH$_2$-Phe-Lys(ivDde)-resin was carried out for 1 h with acetic anhydride (470 µL, 5 mmol) and TEA (700 µL, 5 mmol) in 1.5 mL DMF to give Ac-Phe-Lys (ivDde)-resin.

In a separate control experiment, regular piperidine deprotection was used. To the Fmoc-Lys(ivDde)-resin (10 mg, ~8 µmol) was added piperidine in DMF (20%, 2 mL). The mixture was shaken for 1 min and drained. Another 2 mL of 20% piperidine was added and the mixture was shaken for 15 min. The resin was then washed, coupled with Fmoc-Phe as described above to give Ac-Phe-Lys(ivDde)-resin.

Ac-Phe-Lys-resin. To Ac-Phe-Lys(ivDde)-resin (10 mg) was added 2-(2-nitrophenyl)propoxycarbonyl hydrazine (95.6 mg, 400 µmol, 200 mM) in 2 mL DMF. The UV lamp (350-450 nm) was directly pointed towards the reaction vessel and turned on for 10 min. The resin was then washed with DMF and the deprotection reaction was monitored by ninhydrin test and repeated as necessary. Finally, the resin was washed with DMF (5×1 mL), 10% DIPEA in DMF (5×1 mL), and DCM (5×1 mL).

In a separate control experiment, to Ac-Phe-Lys(ivDde)-resin (10 mg) was added hydrazine monohydrate (40 µL, 824 µmol, 412 mM) in 2 mL DMF. After 5 min agitation, the solution removed by suction and a fresh 2% hydrazine monohydrate solution was added for an additional 7 min. The resin was washed with DMF (5×1 mL), 10% DIPEA in DMF (5×1 mL), and DCM (5×1 mL).

Ac-Phe-Lys-OH and Ac-Phe-Lys(ivDde)-OH. Cleavage of the synthesized peptides from resin was accomplished using 1% TFA in DCM (twice resin bed volume) for ~2 min. For each sample, aliquots were dried on a speed-vac and directly used for HPLC or MALDI-TOF analysis. HPLC Column was reverse phase (Waters RP-C18, 8C1810µ. Elute solvents were water and acetonitrile containing 0.1% or 0.08% TFA, respectively. The gradient used was 15 to 95% of water in acetonitrile in 16 min with a flow rate of 3 mL/min. Ac-Phe-Lys(ivDde)-OH by photogenerated piperidine synthesis, Rt=8.55 min; piperidine synthesis, Rt=8.57 min. Ac-Phe-Lys-OH, by photogenerated piperidine and hydrazine synthesis, Rt=3.55 min; regular synthesis (piperidine and hydrazine) Rt=3.54 min. $^1$H NMR (300 MHz, DMSO d$_6$): Ac-Phe-Lys(ivDde)-OH synthesized using either photogenerated piperidine or piperidine gave identical NMR spectra; δ 13.60 (s, 1H, NH), 12.62 (br s, COOH), 8.27 (d, J=8.1 Hz, 1H, CONH), 8.06 (d, J=7.8 Hz, 1H, CONH), 7.22 (m, 5H, ArH), 4.51 (m, 1H, αCH), 4.18 (m, 1H, αCH), 3.38 (m, Phe βCH$_2$, Lys εCH$_2$), 3.00 (m, 2H, ivDde CH$_2$), 2.25 (s, 4H, ivDde CH$_2$), 1.80 (m, βCH$_2$), 1.72 (s, CH$_3$), 1.58 (m, ivDde CH, Lys δCH$_2$), 1.40 (m, 2H, γCH$_2$), 0.92 (s, 6H, CH$_3$), 0.88 (s, 6H, CH$_3$). Ac-Phe-Lys-OH (both dipeptides synthesized using either photogenerated piperidine and hydrazine versus piperidine and hydrazine gave identical NMR spectra), δ 12.67 (br s, COOH), 8.31 (d, J=7.8 Hz, 1H, CONH), 8.09 (d, J=7.8 Hz, 1H, CONH), 7.65 (s, NH$_3^+$), 7.22 (m, 5H, ArH), 4.51 (m, 1H, αCH), 4.18 (m, 1H, αCH), 3.34 (m, 1H, Phe βCH), 2.98 (m, 1H, Phe βCH), 2.74 (m, 2H, εCH$_2$), 1.72 (s, 3H, CH$_3$), 1.58 (m, βCH$_2$), 1.55 (m, δCH$_2$), 1.34 (m, γCH$_2$). Mass analysis (MALDI-TOF): calculated for Ac-Phe-Lys(ivDde)-OH 541.7, found 541.9 for that by photogenerated piperidine synthesis and found 541.8 for that by piperidine; calculated for Ac-Phe-Lys-OH 335.4, found 335.5 for that by photogenerated piperidine and hydrazine, found 335.5 for that by piperidine and hydrazine.

Example X

Tyr-Gly-Gly-Phe-Leu-OH Synthesis Using PGB

Wang resin (30 mg, 30 µmol) in DMF/DCM (v/v 1/1, unless otherwise specified, 1 mL) was treated with Fmoc-Leu (180 µmol) in the presence of coupling reagents DIC (14 µL, 90 µmol) and DMAP (0.37 mg, 3 µmol) for 2 h. The Fmoc-Leu-resin was washed thoroughly with DMF and DCM, dried under vacuum, and stored in a dry place. To this resin (10 mg, 10 µmol) was added 2-(2-nitrophenyl)propoxycarbonyl piperidine in 2 mL of DMF (58.4 mg, 200 µmol, 100 mM). The UV lamp (365 nm) was directly pointed towards the reaction vessel and turned on for 15 min. The resin was extensively washed with DMF, dioxane/water (2:1), DMF, and DCM. After washing, a ninhydrin test was performed to confirm the presence of free amino groups.

In a separate experiment, to Fmoc-Leu-resin was added piperidine in DCM (20%, 2 mL). The mixture was shaken for 1 min and drained. Another 2 mL of 20% piperidine was added and this time the mixture was shaken for 15 min. The resin was then washed as described above.

To the Fmoc-Leu resin was added Fmoc-Phe (40 µmol) in DCM/DMF (1 mL) and DIC (3 µL, 20 µmol). The coupling reaction was continued for 2 h and repeated if a ninhydrin test gave positive amino group reading. The resin was then washed with DCM/DMF. The steps of coupling and deprotection using either photogenerated piperidine or piperidine were repeated until the completion of the pentapeptide synthesis. The coupling steps were carried out as described using an appropriate Fmoc-amino acid. Tyr(tBu)-Gly-Gly-Phe-Leu-resin synthesized using either photogenerated piperidine or piperidine were treated with TFA/water (95:5) for 3 h for removal of the tBu group and cleavage from resin. The collected samples were injected on to HPLC and the retention times for Tyr-Gly-Gly-Phe-Leu-OH were 9.19 or 9.15 min, respectively (FIG. 12). Synthesis yields were calculated from the integration of HPLC peaks monitored at 214 nm and were 89% and 74% (stepwise yields were 93 and 97%) for the synthesis using either photogenerated piperidine or piperidine, respectively. Mass analysis (MALDI-TOF, external calibration on Angiotensin II 1046.54 g/mol): calculated for YGGFL C$_{28}$H$_{37}$N$_5$O$_7$ 555.62, found 555.65 (synthesized using photogenerated piperidine) and 556.11 (synthesized using piperidine). Mass analysis of the crude product also indicates the presence of Phe-Leu-OH (278.37), Gly-Gly-Phe-Leu-OH (392.44), and Tyr(tBu)-Gly-Gly-Phe-Leu-OH (613.21) in both of the synthesis using either photogenerated piperidine or piperidine.

Example XI

Synthesis of 2-(2-nitrophenyl)propyl trifluoroacetate (FIG. 4A, eq. 4, R=105a). To a solution of 2-(2-nitrophenyl)propanol (0.219 g, 1.20 mmol) and triethylamine (0.33 mL, 2.4 mmol) in 3 mL THF, trifluoroacetic anhydride (0.27 mL, 1.92 mmol) was added slowly in drops. The reaction was monitored by TLC using 2:7 ethyl acetate:hexane. After 3.5 h the reaction mixture was quenched with water. It was then extracted with DCM and the organic layer was washed with water and brine and then dried over anhydrous sodium sulfate. On evaporating the organic layer 420 mg of crude product was obtained. $^1$H NMR (300 MHz, CDCl$_3$) δ(ppm): 7.80 (d, 1H, Ar—H), 7.61 (t, 1H, Ar—H), 7.55-7.36 (m, 2H, Ar—H), 4.52 (d, 2H, CH$_2$), 3.79 (q, 1H, CH), 1.41 (d, 3H, CH$_3$). $^1$H NMR (300 MHz, DMF-d$_7$): δ 7.85 (d, 1H, Ar—H), 7.68 (m, 2H, Ar—H), 7.47 (t, 1H, Ar—H), 4.62 (d, 2H, CH$_2$), 3.63 (q, 1H, CH), 1.32 (d, 3H, CH$_3$).

Example XII

Synthesis of 2-(2-nitrophenyl)propoxyl β-cyanoethyl diisopropyl phosphoramidite (NPPO-ppa). To a solution of 2-(2-nitrophenyl)propanol (0.530 g, 2.91 mmol) and triethylamine (1.63 mL, 11.6 mmol) in 9 mL DCM, 2-cyanoethyl diisopropyl-chlorophosphoramidite (0.98 mL, 4.37 mmol) was added slowly in drops. The reaction was monitored by TLC using 2:7 ethyl acetate:hexane. After 2 h the reaction mixture was cooled in an ice bath and 4 mL triethylamine and 12 mL saturated NaHCO$_3$ in cold water were added. It was then extracted with DCM and the organic layer was dried over anhydrous sodium sulfate. On evaporating this solution crude product was obtained, which was purified on silica gel column eluting with ethyl acetate:hexane (1:2, 0.2% TEA) to obtain 0.418 g (37%) of NPPOC-ppa. The purified product was dried under vacuum. $^1$H NMR (300 MHz, DMSO-d$_6$) δ (ppm): 7.76 (m, 1H), 7.63 (t, 2H), 7.34 (m, 1H), 3.74-3.36 (m, 6H), 2.69-2.62 (m, 2H), 1.26-1.23 (m, 3H), 1.06-0.92 (m, 9H); $^{31}$P NMR (CDCl$_3$) δ (ppm): 148.48, 148.41.

Example XIII

Synthesis of N-methylsulfonyloxynaphthalimide (FIG. 4B, R=107)

The compound N-hydroxy-1,8-naphthalimide (300 mg, 1.40 mmol) and t-BuOK (166 mg, 1.40 mmol) were dissolved in dry THF (10 mL) under N$_2$. After the reaction mixture was stirred for 1 h at r.t., the solvent was removed in vacuo to give 323 mg (1.37 mmol, 98% yield) of a red solid that was directly used for next reaction step.

A solution of methanesulfonic acid (30 μL, 0.41 mmol) in anhydrous dimethoxymethane (150 μL) was added to a cold solution (−15° C., dry ice/ethylenediol) of sodium N-hydroxynaphthalimide (100 mg, 0.42 mmol) in anhydrous dimethoxymethane (5 mL) over a period of 4 min with stirring and under N$_2$. After 15 min, the reaction mixture was allowed to warm up to room temperature and the stirring was continued for 1 h. DCM (50 mL) was added to the reaction mixture and the resulting solution was washed with 2% aqueous sodium bicarbonate and water. The organic portion was dried over Na$_2$SO$_4$ and filtered. The solvent was removed in vacuo and 90 mg of a yellow powder was obtained. Recrystallization of the product from DCM/hexane yielded 80 mg (0.28 mmol, 67% yield) of N-methanesulfonyloxynaphthalimide. $^1$H-NMR (300 MHz, DMSO-d$_6$) δ 8.53 (d, J=7.5 Hz, 2H, Ar—H), 8.32 (d, J=8.7 Hz, 2H, Ar—H), 7.78 (t, J=8.4 Hz, 2H, Ar—H), 3.54 (s, 3H, CH$_3$). TLC: 20% ethyl acetate in hexanes, R$_f$=0.2.

Example XIV

Synthesis of 2-(3,4-methylenedioxy-6-nitrophenyl)-propoxycarbonyl piperidine (FIG. 4A, eq. 4, R=101)

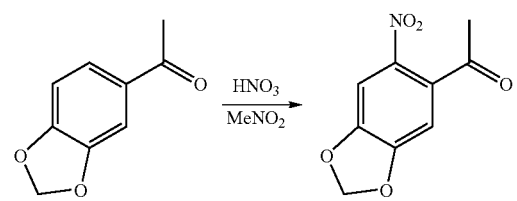

Preparation of 3,4-(methylenedioxy)-6-nitroacetophenone. To 3,4-(methylenedioxy)-acetophenone (2.70 g, 17.5 mmol) in 30 mL CH$_3$NO$_2$ at r.t. was added HNO$_3$ (6.9 mL, 105 mmol) dropwise in 30 min. The solution was stirred for additional 2 h. The reaction mixture was carefully neutralized by the addition of saturated aqueous NaHCO$_3$ solution and then extracted with DCM. The combined organic phase was dried overnight over anhydrous Na$_2$SO$_4$. The solvent was removed in vacuo and the residue was purified by silica gel chromatography (eluant: AcOEt/Hex, 1/2, v/v) to afford 3,4-(methylenedioxy)-6-nitroacetophenone (2.80 g, 82%) as light yellow solid. $^1$H-NMR (300 MHz, CDCl$_3$): δ 7.56 (s, 1H, Ar—H), 6.76 (s, 1H, Ar—H), 6.19 (s, 2H, CH$_2$), 2.50 (s, 3H, CH$_3$). TLC: 33% ethyl acetate in hexane, Rf=0.5.

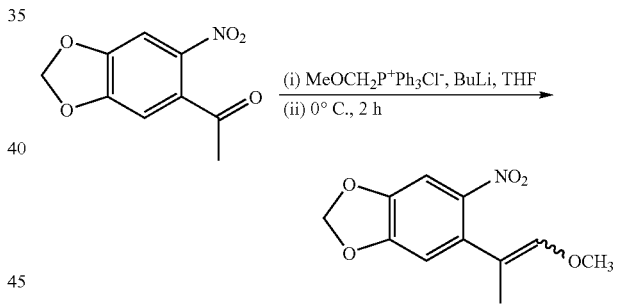

Preparation of 2-(3,4-methylenedioxy-6-nitrophenyl)propyl enol methyl ether. BuLi (2.0 M in cyclohexane, 10 mL, 20 mmol) was added to 20 mL THF. The solution was stirred under nitrogen atmosphere at −10° C. To this solution was added methoxymethyltriphenylphosphonium chloride (6.80 g, 20 mmol) in four portions. After 15 min stirring, the nitrated ketone, 3,4-(methylenedioxy)-6-nitroacetophenone (2.10 g, 10 mmol) in THF (20 mL) was added in drops for 30 min. The reaction was nearly complete in 2 h (monitored by TLC, eluant: AcOEt/Hex, 1/7, v/v). The crude reaction mixture was poured onto ice/water and THP was evaporated. The residue was dissolved in DCM, the organic phase was collected and dried over anhydrous Na$_2$SO$_4$ overnight, and the solvent was evaporated in vacuo. Purification by silica gel chromatography (eluant: AcOEt/Hexane, 10/90, v/v) provided 2-(3,4-methylenedioxy-6-nitrophenyl)-propyl enol methyl ether (mixture of E,Z isomer, 1.30 g, 60%). $^1$H-NMR (300 MHz, CDCl$_3$): δ 7.40 (s, 0.4H, Ar—H), 7.37 (s, 0.6H, Ar—H), 6.70 (s, 0.4H, Ar—H), 6.68 (s, 0.6H, Ar—H), 6.08 (s, 2H, CH$_2$), 5.96 (d, J=1.8 Hz, 0.6H, CH), 5.93 (d, J=1.8 Hz, 0.4H, CH), 3.67 (s, 1.8H, CH$_3$), 3.50 (s, 1.2H, CH$_3$), 1.87 (d, J=1.2 Hz, 1.2H, CH₃), 1.85 (d, J=1.2 Hz, 1.8H, CH₃). TLC: 12% ethyl acetate in hexanes, Rf=0.3.

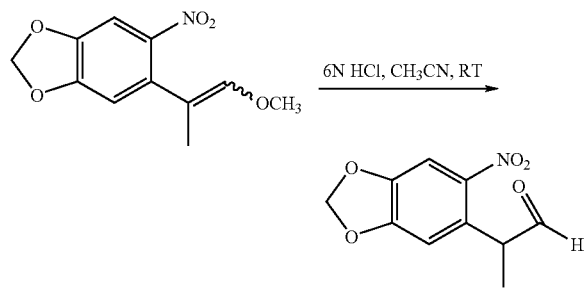

Preparation of 2-(3,4-methylenedioxy-6-nitrophenyl)propyl aldehyde. 2-(3,4-methylenedioxy-6-nitrophenyl)propyl enol methyl ether (1.29 g, 6 mmol) was dissolved in CH₃CN/HCl (6 N, 1/1, v/v, 50 mL) and the solution was stirred for 1.5 h at r.t., and the mixture was slowly poured into a solution saturated with NaHCO₃. After extraction with DCM, the organic phase was dried over anhydrous MgSO₄. The solvent was removed in vacuo and 2-(3,4-methylenedioxy-6-nitrophenyl)propyl aldehyde was obtained as a yellow oil (0.89 g, 74%). ¹H-NMR (300 MHz, CDCl₃): δ 9.74 (s, 1H, CH), 7.54 (s, 1H, Ar—H), 6.70 (s, 1H, Ar—H), 6.13 (s, 2H, CH₂), 4.32 (q, J=7.2 Hz, 1H, CH), 2.50 (d, J=7.2 Hz, 3H, CH₃). TLC: 12% ethyl acetate in hexanes, Rf=0.2.

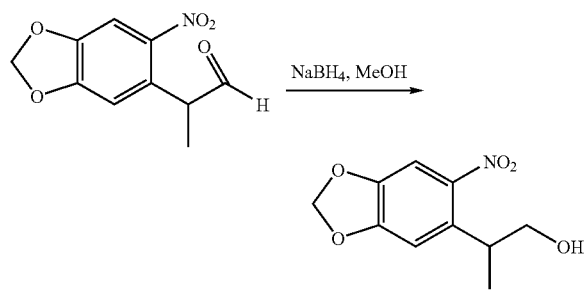

Preparation of 2-(3,4-methylenedioxy-6-nitrophenyl)propanol. To crude 2-(3,4-methylenedioxy-6-nitrophenyl)propyl aldehyde (1.23 g, 5.5 mmol) in anhydrous methanol (20 mL) was added NaBH₄ (250 mg, 6.6 mmol). The reaction was monitored by TLC (eluent: AcOEt/Hex, 1/2, v/v) and complete after 1 h. The mixture was poured into a saturated NH₄Cl aqueous solution and extracted with DCM. The organic phase was dried over anhydrous MgSO₄ and the solvent was removed in vacuo. The residue was purified using silica gel chromatography (eluant: AcOEt/CH₂Cl₂, 1/99, v/v) and provided 2-(3,4-methylenedioxy-6-nitrophenyl)propanol (0.99 g, yield 80%). ¹H-NMR (300 MHz, CDCl₃): δ 7.31 (s, 1H, Ar—H), 6.88 (s, 1H, Ar—H), 6.07 (m, 2H, CH₂), 3.75 (m, 2H, CH₂), 3.64 (m, 1H, CH), 1.77 (s, 1H, OH), 1.27 (d, 3H, CH₃). TLC: 33% ethyl acetate in hexanes, Rf=0.3.

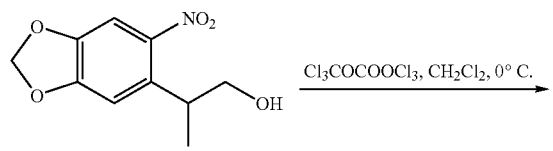

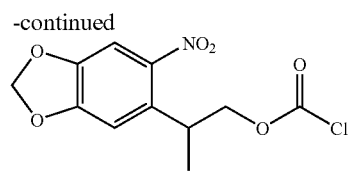

Preparation of 2-(3,4-methylenedioxy-6-nitrophenyl)propoxyl chloroformate. To 2-(3,4-methylenedioxy-6-nitrophenyl)propanol (0.97 g, 4.3 mmol) and DIPEA (750 μL, 4.3 mmol) in dry THF (40 mL) was added to a cold solution (0° C.) of diphosgene (520 μL, 4.3 mmol) in dry THF (40 mL) over a period of 25 min with stirring and under nitrogen. The reaction solution was stirred for additional 30 min and was allowed to warm up to r.t. slowly and continued stirring for 3 h. The solvent was removed in vacuo to give product as light colored oil (0.67 g, 48%). This crude product was directly used in the next step reaction. TLC: 33% ethyl acetate in hexane, Rf=0.7

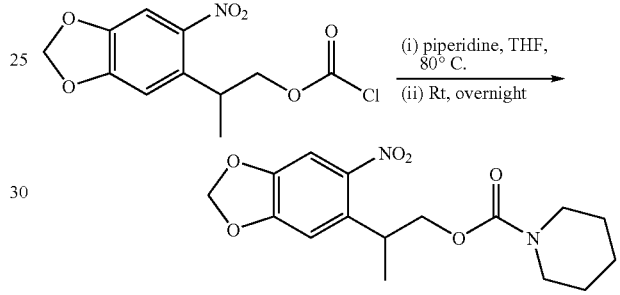

Preparation of 2-(3,4-methylenedioxy-6-nitrophenyl)propoxycarbonyl piperidine. To 2-(3,4-methylenedioxy-6-nitrophenyl)propoxyl chloroformate (650 mg, 2.3 mmol) in dry THF (30 mL) was dropwisely added piperidine (800 μL, 8.1 mmol) in dry THF (20 mL).

The reaction mixture was refluxed for 3 h and then stirred at r.t. overnight. The solvent was evaporated and the residue was dissolved in water and washed with ether four times. The organic extracts were combined and dried over anhydrous Na₂SO₄. The solvent was removed in vacuo and the residue was purified by silica gel chromatography (eluant: AcOEt/Hex, 1/4, v/v). The collected fraction provided 2-(3,4-methylenedioxy-6-nitrophenyl)propoxycarbonyl piperidine (0.61 g, yield 79%). ¹H-NMR (600 MHz, CDCl₃): δ 7.21 (s, 1H, Ar—H), 6.79 (s, 1H, Ar—H), 6.01 (s, 2H, CH₂), 4.12 (m, 2H, CH₂), 3.71 (m, 1H, CH), 3.23 (s, 4H, CH₂), 1.47 (m, 2H, CH₂), 1.38 (s, 4H, CH₂), 1.22 (d, 3H, J=6.6 Hz, CH₃). ¹³C-NMR (150 MHz, CDCl₃): δ 154.86 (OCOR), 151.50 (C ipso to NO₂), 146.13 (C para to NO₂), 143.89 (C para to CH(CH₃) CH₂OCOR), 134.59 (C ipso to CH(CH₃)CH₂OCOR), 106.75 (C ortho to CH(CH₃)CH₂OCOR), 105.02 (C ortho to NO₂), 102.75 (OCH₂O), 68.96 (CH₂OCOR), 44.63 (Cα to ring N), 33.45 (CH), 25.47 (Cβ to ring N), 24.21 (Cγ to ring N), 17.78 (CH₃). TLC: 33% ethyl acetate in hexanes, Rf=0.5.

We claim:
1. A method for forming a biopolymer comprising:
    (a) derivatizing a solid surface with a protected moiety containing at least one protective group
    (b) contacting the solid surface with solution comprising at least one photogenerated reagent precursor and at least one co-reagent;

(c) irradiating the solution thereby generating a photogenerated reagent in at least a portion of the solution such that the protective group is removed from the protected moiety; and (d) coupling a monomer to the deprotected moiety.

2. The method of claim 1 wherein the photogenerated reagent precursor is a photogenerated reagent acid precursor.

3. The method of claim 1 wherein the co-reagent is a base.

4. The method of claim 1 wherein the protected moiety is a protected nucleotide.

5. The method of claim 1 wherein the photogenerated reagent precursor is a photogenerated reagent base precursor.

6. The method of claim 1 wherein the co-reagent is an acid.

7. The method of claim 1 wherein the protected moiety is a protected amino acid.

8. The method of claim 1 wherein the co-reagent is a sensitizer or supersensitizer.

9. A method of deprotecting protected moieties attached to a solid surface and wherein the moieties have one or more protecting group(s) comprising a) contacting the protecting group moieties with a solution comprising one or more PGR-P(s) and one or more co-reagent(s) and b) irradiating the solution to produce one or more PGR(s) wherein the PGR(s) remove the protecting group(s) from the protected moiety.

10. The method of claim 9 wherein the photogenerated reagent precursor is a photogenerated reagent acid precursor.

11. The method of claim 9 wherein the co-reagent is a base.

12. The method of claim 9 wherein the protected moiety is a protected nucleotide.

13. The method of claim 9 wherein the photogenerated reagent precursor is a photogenerated reagent base precursor.

14. The method of claim 9 wherein the co-reagent is an acid.

15. The method of claim 9 wherein the protected moiety is a protected amino acid.

16. The method of claim 9 wherein the co-reagent is a sensitizer or supersensitizer.

* * * * *